(12) United States Patent
Chan et al.

(10) Patent No.: US 9,297,798 B2
(45) Date of Patent: Mar. 29, 2016

(54) THERAPEUTIC APPROACH FOR POLYGLUTAMINE DEGENERATION

(71) Applicant: The Chinese University of Hong Kong, Shatin, New Territories (CN)

(72) Inventors: Ho Yin Edwin Chan, Hong Kong (CN); Ho Tsoi, Hong Kong (CN); Jacky Chi Ki Ngo, Hong Kong (CN); Kwok-Fai Lau, Hong Kong (CN)

(73) Assignee: The Chinese University of Hong Kong, Shatin, N.T., Hong Kong SAR (CN)

( * ) Notice: Subject to any disclaimer, the term of this patent is extended or adjusted under 35 U.S.C. 154(b) by 16 days.

(21) Appl. No.: 14/293,816

(22) Filed: Jun. 2, 2014

(65) Prior Publication Data
US 2014/0357578 A1 Dec. 4, 2014

Related U.S. Application Data

(60) Provisional application No. 61/830,584, filed on Jun. 3, 2013.

(51) Int. Cl.
| | | |
|---|---|---|
| *A61K 38/00* | (2006.01) | |
| *C07K 7/08* | (2006.01) | |
| *C07K 7/06* | (2006.01) | |
| *C07K 14/47* | (2006.01) | |
| *A61K 48/00* | (2006.01) | |
| *A61K 51/08* | (2006.01) | |
| *G01N 33/50* | (2006.01) | |
| *A61K 38/17* | (2006.01) | |
| *G01N 33/68* | (2006.01) | |

(52) U.S. Cl.
CPC ............ *G01N 33/5014* (2013.01); *A61K 38/00* (2013.01); *A61K 38/1709* (2013.01); *A61K 48/00* (2013.01); *A61K 51/08* (2013.01); *A61K 51/088* (2013.01); *C07K 7/08* (2013.01); *C07K 14/47* (2013.01); *G01N 33/6896* (2013.01); *G01N 2800/2821* (2013.01); *G01N 2800/2835* (2013.01)

(58) Field of Classification Search
None
See application file for complete search history.

(56) References Cited

U.S. PATENT DOCUMENTS 5,932,475 A * 8/1999 Bandman et al. .......... 435/320.1
2003/0229019 A1 12/2003 Burke et al.

OTHER PUBLICATIONS

Tsoi et al., Proc. Natl. Acad. Sci. 109:13428-13433 (Aug. 14, 2012).*
NCBI Database, GenBank Accession No. NP_005372, 6 pages (2015).*
Bauer et al., "The pathogenic mechanisms of polygultamine diseases and current therapeutic strategies", *Journal of Neurochemistry*, vol. 110, pp. 1737-1765 (2009).
Boulon et al., "The Nucleolus under Stress", *Molecular Cell*, vol. 40, pp. 216-227 (2010).
Chan et al., "Expanded polyglutamine domain possesses nuclear export activity which modulates subcellular localization and toxicity of polyQ disease protein via exportin-1", *Human Molecular Genetics*, vol. 20, No. 9, pp. 1738-1750 (2011).
Hong et al., "Transcriptional Regulation of the Grp78 Promoter by Endoplasmic Reticulum Stress", *Journal of Biological Chemistry*, vol. 280, No. 17, pp. 16821-16828 (2005).
Hoozemans et al., "Endoplasmic reticulum: The unfolded protein response is tangled in neurodegenreation", *International Journal of Biochemistry & Biology*, vol. 44, pp. 1295-1298 (2012).
Fiszer et al., "RNA toxicity in polyglutamine disorders: concepts, models, and progress of research", *J Mol Med*, vol. 91, pp. 683-691 (2013).
Kalita et al., "Inhibition of nucleolar transcription as a trigger for apoptosis", *Journal of Neurochemistry*, vol. 105, pp. 2286-2299 (2008).
Kouroku et al., "Polyglutamine aggregates stimulate ER stress signals and caspase-12 activation", *Human Molecular Genetics*, vol. 11, No. 13, pp. 1505-1515 (2002).
Kressler et al., "Driving ribosome assembly", *Biochimica et Biophysica Acta*, vol. 1803, pp. 673-683 (2010).
Kryzosiak et al., "Triplet repeat RNA structure and its role as pathogenic agent and therapeutic target", *Nucleic Acids Research*, vol. 40, No. 1, pp. 11-26 (2012).
La Spada et al., "Repeat expansion disease: progress and puzzles in disease pathogenesis", *Genetics*, vol. 11, pp. 247-258 (2010).
Lee et al., "*Drosophila* Short Neuropeptide F Regulates Food Intake and Body Size", *Journal of Biological Chemistry*, vol. 279, pp. 50781-50789 (2004).
Lee et al., The role of ubiquitin linkages on αsynucluein induced-toxicity in a *Drosophila* model of Parkinson's disease, *Journal of Neurochemistry*, vol. 110, pp. 208-219 (2009).
Li et al., "Intracellular degradatino of misfolded proteins in polyglutamine neurodegenerative diseases", *Brain Research Reviews*, vol. 59, pp. 245-252 (2008).
Li et al., "RNA toxicity is a component of ataxin-3 degeneration in *Drosophila*", *Nature*, vol. 453, pp. 1107-1112 (2008).
Lindenboim et al., "Nuclear proteins acting on mitochondria", *Biochimica et Biophysica Acta*, vol. 1813, pp. 584-596 (2011).
Luedtke et al., Fluorescence-Based Methods for Evaluating the RNA Affinity and Specificity of HIV-1 Rev—RRE Inhibitors, *Biopolymer*, vol. 70, pp. 103-119 (2003).
Molhoek et al., "Improved proteolytic stability of chicken cathelicidin-2 derived peptides by d-amino acid substitutions and cyclization", *Peptides*, vol. 32, pp. 875-880 (2011).
Nagai et al., "Prevention of polyglutamine oligomerization and neurodegeneration by the peptide inibitor QBP1 in *Drosophila*", *Human Molecular Genetics*, vol. 12, No. 11, pp. 1253-1260 (2003).
Nagai et al., "Inhibition of Polyglutamine Protein Aggregation and Cell Death by Novel Peptides Identified by Phage Display Screening", *J. Biol. Chem.*, vol. 275, pp. 10437-10422 (2000).

(Continued)

*Primary Examiner* — James H Alstrum Acevedo
*Assistant Examiner* — Thea D'Ambrosio
(74) *Attorney, Agent, or Firm* — Kilpatrick Townsend & Stockton LLP

(57) ABSTRACT

Compositions, methods, and kits are provided for reduction of $(CAG)_n$-RNA mediated toxicity. Compositions, methods, and kits are also provided for treatment of polyglutamine diseases.

22 Claims, 10 Drawing Sheets

(56) References Cited

OTHER PUBLICATIONS

Orr et al., "Trinucleotide Repeat Disorders", *Annu. Rev. Neurosci*, vol. 30, pp. 575-621 (2007).

Popiel et al., "Protein Transduction Domain-mediated Delivery of QBP1 Suppresses Polyglutamine-induced Neurodegeneration In Vivo", *Molecular Therapy*, vol. 15, No. 2, pp. 303-309 (2007).

Popiel et al., "Delivery of the aggregate inhibitor peptide QBP1 into the mouse brain using PTDs and its therapeutic effect on polyglutamine disease mice", *Neuroscience Letters*, vol. 449, pp. 87-92 (2009).

Popiel et al., "The Aggregation Inhibitor Peptide QBP1 as a Therapeutic Molecule for the Polyglutamine Neurodegenerative Diseases", *Journal of Amino Acids*, vol. 2011, article ID 265084, 10 pages (2011).

Shao et a., "Polyglutamine diseases: emerging concepts in pathogenesis and therapy", *Human Molecular Genetics*, vol. 16, pp. R115-R123 (2007).

Shieh et al., "Genes and pathways affected by CAG-repeat RNA-based toxicity in *Drosophila*", *Human Molecular Genetics*, vol. 20, No. 24, pp. 4810-4821 (2011).

Suzuki et al., "Multiple therapeutic peptide vaccines consisting of combined novel cancer testis antigens and anti-angiogenic peptides for patients with non-small cell lung cancer", *Journal of Translational medicine*, vol. 11, 97, pp. 1-10 (2013).

Svensen et al., "Peptides for cell-selective drug delivery", *Trends in Pharmacological Sciences*, vol. 33, No. 4, pp. 186-192 (2012).

Tsoi et al., "CAG expansion induces nucleolar stress in polylutamine diseases", *PNAS*, vol. 109, No. 33, pp. 13428-13433 (2012).

Wang et al., "The impact of the unfolded protein response on human disease", *J. Cell Biol*, vol. 197, No. 7, pp. 857-867 (2012).

Warrick et al., "Ataxin-3 Supresses Polyglutamine Neurodegeneration in *Drosophila* by a Ubiquitin-Associated Mechanism", *Molecular Cell*, vol. 18, pp. 37-48 (2005).

Wojciechowska et al., "Cellular toxicity of expanded RNA repeats: focus on RNA foci", *Human Molecular Genetics*, vol. 20, 3811-3821 (2011).

Wolfe et al, "Amyloid in neurodegenerative diseases: Friend or foe?", *Seminars in cell & Developmental Biology*, vol. 22, pp. 476-481 (2011).

Arribat et al., "A Huntingtin Peptide Inhibits PolyQ-Huntingtin Associated Defects", *PlosOne*, vol. 8, No. 7, pp. e68775, 14 pages, (2013).

* cited by examiner

THERAPEUTIC APPROACH FOR POLYGLUTAMINE DEGENERATION

This application claims priority to U.S. Provisional Application No. 61/830,584, filed Jun. 3, 2013, the contents of which are hereby incorporated by reference in the entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-147-1.TXT, created on Aug. 1, 2014, 12,288 bytes, machine format IBM-PC, MS-Windows operating system, is hereby incorporated by reference in its entirety for all purposes.

BACKGROUND OF THE INVENTION

Many neurodegenerative diseases, including Alzheimer's and Parkinson's diseases, are caused by protein misfolding. Cellular proteins that adopt abnormal pathogenic conformations oligomerize and subsequently form soluble and/or insoluble aggregates in cells causing neuronal dysfunction and death (Wolfe K J, et al. 2011). Polyglutamine (polyQ) diseases belong to the protein misfolding disease group, and it is now known that polyQ toxicity is attributed to the toxic gain-of-function nature of misfolded disease proteins that harbour the expanded polyQ domain (Orr H T, et al. 2007). Unfolded protein response (UPR) is one inducible cellular protective pathway that responds to the emergence of misfolded proteins in cells. It has been reported that this mechanism is involved in neurodegenerative diseases (Hoozemans J J, Scheper W, 2012) including polyglutamine-induced neurodegeneration (Kouroku Y, et al. 2002). Unfolded protein response (UPR) can be mediated by the interaction between misfolded proteins in the endoplasmic reticulum and the molecular chaperone GRP78/BiP, and this interaction would cause the activation of UPR sensors, including activating transcription factor 6 (ATF6), inositol requiring 1 (IRE1) and PKR-like endoplasmic reticulum kinase (PERK) (Wang S, et al. 2012). The induction of GRP78/BiP expression has been used as a reliable indicator of UPR (Hong M, et al. 2005). Upregulation of GRP78/Bip has been observed in polyQ degeneration (Kouroku Y, et al. 2002), this clearly indicates the involvement of protein misfolding in polyQ pathogenesis. However, it is likely that there are other mechanisms involved in polyQ diseases. In particular, the mRNA transcripts that encode the polyQ peptides can play a role in these diseases, especially when the mRNAs encode the polyQ portion as an expanded CAG triplet nucleotide repeat. Such expanded CAG-RNAs are known to contribute to cytotoxicity through mechanisms that are independent of polyQ-mediated cytotoxicity. Accordingly, there is a need to develop methods and compositions for reducing cytotoxicty induced by expanded CAG-RNA molecules.

BRIEF SUMMARY OF THE INVENTION

In one embodiment, the present invention provides an isolated peptide comprising, consisting essentially of, or consisting of SEQ ID NO: 6; or a modified amino acid sequence of SEQ ID NO: 6 in which 1, 2, 3, or 4 amino acids are substituted, deleted, or added, wherein the peptide is not full length NCL. In some cases the isolated polypeptide is conjugated to a detectable label.

In other embodiments, the present invention provides a fusion polypeptide comprising a first portion consisting of an isolated peptide comprising SEQ ID NO: 6; or a modified amino acid sequence of SEQ ID NO: 6 in which 1, 2, 3, or 4 amino acids are substituted, deleted, or added, wherein the peptide is not full length NCL. In further embodiments the fusion protein comprises a second portion comprising a heterologous amino acid sequence, wherein the fusion polypeptide does not comprise the full length NCL.

In some aspects the fusion polypeptide contains a heterologous amino acid sequence at at the N-terminus or the C-terminus of the first portion. In other aspects, the fusion polypeptide contains a heterologous amino acid sequence at the N-terminus and at the C-terminus of the first portion. In some cases, the heterologous amino acid sequence at the N-terminus is different from the heterologous amino acid sequence at the C-terminus. In some aspects, the fusion polypeptide comprises a purification tag, a membrane translocation sequence, or a nucleolar localization signal sequence.

In another embodiment, the present invention provides a composition comprising any one of the foregoing peptides and a pharmaceutically acceptable excipient.

In another embodiment, the present invention provides an isolated nucleic acid encoding any one of the foregoing peptides. In some cases, the isolated nucleic acid contains a modified codon. As used herein, the phrase "modified codon," in the context of a polynucleotide encoding any one of the foregoing peptides, refers to a codon that is different from that found in the naturally occurring sequence. Typically, the modified codon does not alter the amino acid sequence of the encoded peptide. In some cases, the codon modification is a codon optimization. For example, one or more codons may be optimized to increase expression in a host cell.

In another embodiment, the present invention provides an expression cassette comprising a nucleic acid encoding any one of the foregoing peptides. In some aspects, the expression cassette contains a promoter (e.g., a heterologous promoter) operably linked to a polynucleotide encoding any one of the foregoing peptides. The present invention also provides an isolated host cell comprising the provided expression cassette. The present invention also provides a composition comprising a nucleic acid encoding any one of the foregoing peptides, or an expression cassette comprising a nucleic acid encoding any one of the foregoing peptides and a pharmaceutically acceptable excipient.

In another embodiment, the present invention provides a kit for inhibiting proliferation of a cell, or reducing cytotoxicity of a cell, the kit comprising the composition of any one of the foregoing peptides, nucleic acids, or expression cassettes.

In another embodiment, the present invention provides a kit for identifying an inhibitor of $(CAG)_n$-mediated toxicity comprising a polynucleotide sequence comprising at least 10 repeats of CAG triplet nucleotides and a composition that binds the polynucleotide sequence. In some aspects, the polynucleotide is fluorescently labeled. In some aspects the composition is any one of the foregoing peptides. In some aspects, the kit contains is nucleolin, or a portion of nucleolin capable of binding a polynucleotide comprising at least 10, 20, 30, 40, 50, 60, 70, 78, or 100 CAG (SEQ ID NO:16) triplet nucleotides.

In one embodiment, the present invention provides a method of reducing $(CAG)_n$-mediated toxicity in a cell, the method comprising contacting the cell with an effective amount of an inhibitor that inhibits the binding of nucleolin to a $(CAG)_n$ triplet nucleotide repeat RNA. In some aspects, the (CAG)$_n$ triplet nucleotide repeat RNA comprises at least 10, 20, 30, 40, 50, 60, 70, 78, or 100 CAG (SEQ ID NO:16) triplet nucleotides. In some cases, the composition binds the (CAG)$_n$ triplet nucleotide repeat RNA. In some cases, the cell comprises nucleic acid encoding MJD$_{CAGn}$, or DsRed$_{CAGn}$, wherein each n is independently selected from about 10, 20, 30, 40, 50, 60, 70, 78, and 100.

In some aspects, the cell is in a patient's body. In some cases, the method further comprises reducing (CAG)$_n$-mediated toxicity in a subject suffering from Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17. In some cases, the contacting step is performed by oral administration, or subcutaneous, intramuscular, intravenous, intraperitoneal, or intratumor injection.

In some aspects, the composition comprises a peptide. In some aspects, the composition is a peptide comprising an amino acid sequence derived from an RNA-recognition motif of nucleolin. In some aspects, the inhibitor is a peptide of less than 10, 12, 15, 20, 25, 30, 35, 50, 75, 100, 150, 200, 250, 350, 500, 700, or 714 amino acids in length. In some aspects, The method of claim 16, wherein the inhibitor is a peptide derived from an RNA-recognition motif of nucleolin. In some cases, the peptide consists of SEQ ID NO: 6; or consists of the amino acid sequence of SEQ ID NO: 6 in which 1, 2, 3, or 4 amino acids are substituted, or deleted. In some cases, the peptide composition is not full-length nucleolin. In some aspects, the composition is a peptide, and the contacting comprises overexpressing a gene encoding the composition.

In some aspects, the method further comprises contacting the cell with a composition that inhibits poly-Q mediated toxicity. In some cases, the composition that inhibits poly-Q mediated toxicity comprises or consists of a polypeptide having the amino acid sequence of SEQ ID NO:15 (QBP1). In some cases, the composition that inhibits poly-Q mediated toxicity comprises or consists of a polypeptide having the amino acid sequence of SEQ ID NO:15 (QBP1) in which 1, 2, 3, or 4 amino acids are substituted, or deleted.

In another embodiment, the present invention provides a method of identifying compositions for treatment of (CAG)$_n$-mediated toxicity, the method comprising: contacting a test cell with a candidate composition; and assaying an indicator of (CAG)$_n$-mediated toxicity to determine a level of (CAG)$_n$-mediated toxicity.

In some aspects, the method further comprises comparing the level of (CAG)$_n$-mediated toxicity in the test cell to the level of (CAG)$_n$-mediated toxicity in a control cell in which (CAG)$_n$-mediated toxicity has not been treated. In some aspects, the method further comprises comparing the level of (CAG)$_n$-mediated toxicity in the test cell to the level of (CAG)$_n$-mediated toxicity in a control cell in which (CAG)$_n$-mediated toxicity has been treated with a compound known to inhibit (CAG)$_n$-mediated toxicity.

In some aspects, the test cell comprises a CAG triplet nucleotide repeat and exhibits (CAG)$_n$-mediated toxicity. In some cases, the (CAG)$_n$ triplet nucleotide repeat comprises at least 10, 20, 30, 40, 50, or 60 CAG (SEQ ID NO:17) triplet nucleotides. In some cases, the test cell comprises nucleic acid encoding MJD$_{CAG}$, or DsRed$_{CAG}$.

In some aspects, the indicator of (CAG)$_n$-mediated toxicity is binding of nucleolin to an rRNA promoter upstream control element (UCE). In some cases compositions that promote binding of nucleolin to the UCE relative to a control cell are identified as treating (CAG)$_n$-mediated toxicity.

In some aspects, the indicator of (CAG)$_n$-mediated toxicity is hypermethylation of the rRNA UCE. In some cases, the compositions that inhibit hypermethylation of the UCE relative to a control cell are identified as treating (CAG)$_n$-mediated toxicity.

In some aspects, the indicator of (CAG)$_n$-mediated toxicity is transcription of rRNA. In some cases, compositions that promote transcription of rRNA relative to an untreated control cell exhibiting (CAG)$_n$-mediated toxicity are identified as treating (CAG)$_n$-mediated toxicity.

In some aspects, the indicator of (CAG)$_n$-mediated toxicity is nucleolar stress. In some cases, the nucleolar stress is exhibited by p53 inhibition, caspase 3 activation, reduction in rRNA levels, or induction of GRP78/BiP expression.

DETAILED DESCRIPTION OF THE INVENTION

I. Introduction

Figure 1:
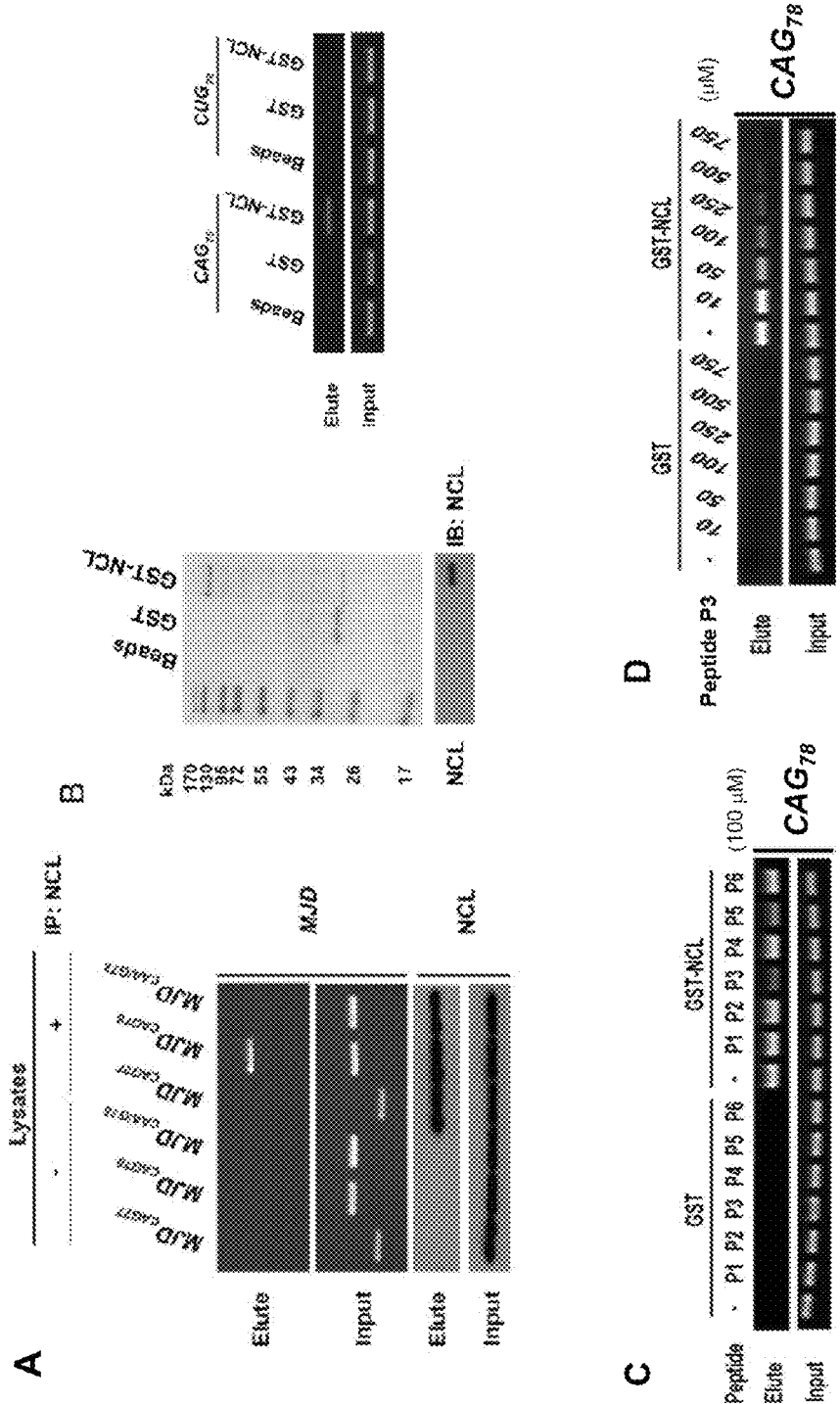
FIG. 1. Illustrates the physical interaction between Nucleolin (NCL) and expanded CAG RNAs. A. Nucleolin binds CAG RNAs derived from MJD message containing CAG repeats in cells but does not bind MJD message containing CAA/G repeats. B-D. Nucleolin binds expanded CAG RNAs in vitro. B. Purified GST-NCL protein was tested for binding to in vitro transcribed RNAs (CAG$_{78}$ (SEQ ID NO:18) and CUG$_{78}$ (SEQ ID NO:19)). C. Binding of expanded CAG RNA to NCL is tested in the presence of 100 µM of synthetic NCL peptides P1-P6 (SEQ ID NOs. 1-6 respectively). D. Peptide P3 disrupts the interaction between purified NCL and expanded CAG RNA in a dose dependent manner. "-" denotes that no synthetic peptide was added to the binding reaction.

In 2008, Li et al. reported the contribution of toxic expanded CAG RNAs to the pathogenesis of polyQ diseases (Li L B, et al. 2008). Progressive neural degeneration was still observed when the expanded CAG repeat sequence was isolated from the disease gene and expressed as an untranslated RNA in vivo (thus ensuring no expanded polyQ domain would be translated) (Li L B, et al. 2008). This finding indicated that expanded CAG RNAs per se are neurotoxic (Wojciechowska M, et al. 2011). Sixteen neurological disorders are currently known to be caused by this common CAG trinucleotide expansion mechanism (Orr H T, et al. 2007). Mechanisms that govern expanded CAG RNA toxicity have received increasing attention, and different aspects of expanded CAG RNA toxicity in polyQ disease have been reported in recent years (Wojciechowska M, et al. 2011).

The nucleolus is the production site of ribosome subunits, and dysregulation of ribosome biogenesis has been shown to cause disease (Kressler D, et al. 2010). RNA polymerase I (pol I) is responsible for the transcription of ribosomal RNA precursors (pre-rRNA), and rRNA is an essential component of the ribosome, a ribonucleoprotein complex responsible for protein translation. Inhibition of pre-rRNA transcription has been shown to cause apoptosis in neurons (Kalita K, et al. 2008).

"Nucleolar stress" is a term used to describe a signaling pathway through which the nucleolus communicates with other subcellular compartments (Boulon S, et al. 2010), including the mitochondria (Lindenboim L, et al. 2011), to induce apoptosis. It is an effective mechanism used to eliminate cells that are incapable of performing protein synthesis efficiently due to ribosome biogenesis defects, including neurons. A link between nucleolar stress and RNA toxicity in polyQ diseases has recently been demonstrated (Tsoi H, et al. 2012).

Nucleolin (NCL), a nucleolar protein that regulates rRNA transcription, interacts directly and specifically with expanded CAG RNAs (FIGS. 1A and B), and such binding is mediated by the RNA-recognition motifs (RRMs) of NCL (Tsoi H, et al. 2012). This RNA/protein interaction prevents NCL protein from binding to the upstream control element (UCE) of the rRNA promoter, which results in UCE DNA hypermethylation. Subsequently, rRNA transcription is downregulated. This results in stabilization of p53 protein and concentration of p53 in the mitochondria of cells experiencing nucleolar stress activation (Boulon S, et al. 2010).

Additionally, apoptosis is induced in an expanded CAG RNA toxicity cell model as evidenced by cytochrome c release from the mitochondria and caspase activation (Tsoi H, et al. 2012). This provides in vivo evidence that expanded CAG RNAs trigger nucleolar stress, which in turn induces apoptosis. Moreover, overexpression of NCL can reverse nucleolar stress induction in vivo (Tsoi H, et al. 2012). This thus opens up an avenue for therapeutic developments to counteract expanded CAG RNA toxicity.

Various approaches have been developed to minimize the toxic effects of both protein and RNA toxicities in polyQ diseases. For instance, one well-studied peptide inhibitor of polyQ protein toxicity is QBP1 peptide (Popiel H A, et al. 2007; Nagai Y, et al. 2003). This 11 amino acid-peptide binds to expanded monomeric polyQ protein and inhibits the beta-sheet conformation transition of the disease protein. It has been reported that the QBP1 peptide is capable of suppressing polyQ protein toxicity both in vitro and in vivo (See, Popiel H A, et al. 2007; Nagai Y, et al. 2003; U.S. Pat. No. 6,632,616).

Recently, Krzyzosiak et al. (2012) discussed various therapeutic strategies that may be used to interfere with toxic RNA species including expanded CAG RNAs. For instance, small-molecule compounds that are capable of interacting specifically with expanded trinucleotide repeat RNAs can be used to prevent toxic RNA species from interacting with cellular proteins in cells. Thus, proteins that display strong affinity toward toxic RNA species will not be prevented from performing their normal cellular functions.

II. Definitions

The term "inhibiting" or "inhibition," as used herein, refers to any detectable negative effect on a target biological process, such as the binding between NCL and expanded CAG-RNA, or on other processes including nucleolar stress, hypermethylation of the upstream control element (UCE) of rRNA, reduction of rRNA transcription, and reduction in CAG-RNA induced apoptosis. Typically, an inhibition is reflected in a decrease of at least 10%, 20%, 30%, 40%, or 50% in NCL: expanded CAG-RNA binding, or any one of the downstream parameters mentioned above, when compared to a control.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N.Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a core amino acid sequence responsible for expanded CAG-RNA binding has at least 80% identity, preferably 85%, 90%, 91%, 92%, 93, 94%, 95%, 96%, 97%, 98%, 99%, or 100% identity, to a reference sequence, e.g., one of SEQ ID NOs:1-14), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

As used herein, the term "nucleolin" or "NCL" refers to the nucleolin protein. Exemplary nucleolin proteins include those of the Chinese Hamster (Genbank Accession No. AAA36966.1), the golden hamster (Genbank Accession No. P08199.2), the Norwegian Rat (Genbank Accession No. EDL75577.1), the house mouse (Genbank Accession No. EDL40222.1), and human nucleolin (Genbank Accession No. EAW70962.1). In some embodiments of this invention, peptides derived from NCL are provided for treatment of expanded CAG-RNA mediated cytotoxicity or polyQ disease. In any case, such peptides are less than full length NCL. For example, such peptides can be shorter in length, e.g., less than 714 amino acids in length or less than about 75, 100, 150, 200, 250, 300, 350, 400, 500, 600, or 700 amino acids in length.

As used herein, a "polypeptide comprising an NCL RNA recognition motif (RRM) domain" refers to a polypeptide containing a core amino acid sequence that generally corresponds to the amino acid sequence of an RNA recognition motif of nucleolin (NCL). Nucleolin contains three RRM domains, including:

RRM1, SEQ ID NO: 1:
F N L F I G N L N P N K S V A E L K V A I S E P F
A K N D L A V V D V R T G T N R K F G Y V D F E S
A E D L E K A L E L T G L K V F G N E I K L E K P
K G;

RRM2, SEQ ID NO: 2:
R T L L A K N L S F N I T E D E L K E V F E D A L
E I R L V S Q D G K S K G I A Y I E F K S E A D A
E K N L E E K Q G A E I D G R S V S L Y Y T G E;
and RRM3, SEQ ID NO: 3:
K T L V L S N L S Y S A T E E T L Q E V F E K A T
F I K V P Q N Q Q G K S K G Y A F I E F A S F E D
A K E A L N S C N K M E I E G R T I R L E L Q G P These core amino acid sequences may contain some variations such as amino acid deletion, addition, or substitution, but should maintain a substantial level sequence homology (e.g., at least 80%, 85%, 90%, 95%, or higher sequence homology) to SEQ ID NO:1, SEQ ID NO:2, or SEQ ID NO. 3.

Moreover, RRM2 domains, and homologs thereof, are capable of binding RNA containing 1, 2, 3, 4, 5, 10, 15, 20, 25, 30, 35, 40, 50, 60, 75, or more CAG triplet nucleotide repeats. In addition to this core sequence that is responsible for the polypeptide's ability to bind to expanded CAG-RNA, one or more amino acid sequences of a homologous origin (e.g., additional sequence from the same protein, NCL) or a heterologous origin (e.g., sequence from another unrelated protein) can be included in the polypeptide.

Some examples of the "polypeptide comprising an NCL RRM domain" include SEQ ID NO:1, SEQ ID NO: 2, and SEQ ID NO: 3. However, as used herein, "polypeptide comprising an NCL RRM domain" does not include the full length wild-type NCL. For example, in some cases, the "polypeptide comprising an NCL RRM domain" can be shorter than a full length NCL RRM domain, e.g., less than about 25, 30, 40, 50, 60, 70, 80, 90, or 100 amino acids in length. Optionally, one or more peptides of a heterologous origin, for example, an affinity or epitope tag (such as a GST tag), can be included in the polypeptide at either or both ends to facilitate purification, isolation, or immobilization of the polypeptide. If a heterologous amino acid sequence is included at both ends, each end can be fused to the same heterologous amino acid sequence, or each end can be fused to a different sequence.

Similarly, a "polypeptide comprising an amino acid sequence derived from an RNA-recognition motif of nucleolin," a "polypeptide comprising an amino acid sequence derived from an RRM domain of nucleolin," or a "polypeptide comprising an RRM-related amino acid sequence" refers to a polypeptide containing a core amino acid sequence that generally corresponds to an amino acid sequence of one of SEQ ID NOs: 4-14.

P1,
(SEQ ID NO: 4)
AKNLPYK,

P2,
(SEQ ID NO: 5)
RVASKDGKSKGIAD,

P3,
(SEQ ID NO: 6)
DGKSKGIAYIEFK,

P4,
(SEQ ID NO: 7)
DALEIRLVSQRGK,

P5,
(SEQ ID NO: 8)
VPQNQNGKSKGYAF,
and

P6,
(SEQ ID NO: 9)
REIEGRAIR.

Exemplary peptides further include:
P3MT1,
(SEQ ID NO: 10)
DGASKGIAYIEFK

P3MT2,
(SEQ ID NO: 11)
DGKSAGIAYIEFK

P3MT3/MTa,
(SEQ ID NO: 12)
DGKSKGIAAIEFK

P3MT4/MTb,
(SEQ ID NO: 13)
DGKSKGIAYIEAK;
and

P3MT5/MTc,
(SEQ ID NO: 14)
DGKSKGIAAIEAK

These core amino acid sequences may contain some variations such as amino acid deletion, addition, or substitution, but should maintain a substantial level sequence homology (e.g., at least 80%, 85%, 90%, 95%, or higher sequence homology) to any one of SEQ ID NOs:4-14.

Moreover, P3 peptides, and homologs thereof, are capable of binding RNA containing 1, 2, 3, 4, 5, 10, 15, 20, 25, 30, 35, 40, 50, 60, 75, or more CAG triplet nucleotide repeats. In addition to this core sequence that is responsible for the polypeptide's ability to bind to expanded CAG-RNA, one or more amino acid sequences of a homologous origin (e.g., additional sequence from the same protein, NCL) or a heterologous origin (e.g., sequence from another unrelated protein) can be included in the polypeptide.

Some examples of the "polypeptide comprising an amino acid derived from an RNA-recognition motif of nucleolin" include SEQ ID NOs: 4-14. However, as used herein, "polypeptide comprising an amino acid derived from an RNA-recognition motif of nucleolin" does not include the full length wild-type NCL. For example, the "polypeptides comprising an amino acid derived from an RNA-recognition motif of nucleolin" can be shorter than full length NCL, e.g., less than 714 amino acids in length or less than about 10, 12, 15, 20, 25, 30, 35, 50, 75, 100, 150, 200, 250, 300, 350, 400, 500, 600, or 700 amino acids in length. Optionally, an affinity or epitope tag (such as a GST tag) can be included in the polypeptide to facilitate purification, isolation, or immobilization of the polypeptide.

"Translocation sequence" or "transduction sequence" refers to a peptide or protein (or active fragment or domain thereof) sequence that directs the movement of a protein from one cellular compartment to another, or from the extracellular space through the cell or plasma membrane into the cell. Examples include the TAT transduction domain (see, e.g., S. Schwarze et al., Science 285 (Sep. 3, 1999); penetratins or penetratin peptides (D. Derossi et al., Trends in Cell Biol. 8, 84-87); and Herpes simplex virus type 1 VP22 (A. Phelan et al., Nature Biotech. 16, 440-443 (1998). Translocation peptides can be fused (e.g. at the amino or carboxy terminus), conjugated, or coupled to a compound of the present invention, to, among other things, produce a conjugate compound that may easily pass into target cells, or through the blood brain barrier and into target cells.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) *Nature* 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

The term "$(CAG)_n$-mediated toxicity," "expanded CAG-RNA mediated cytotoxicity" and the like, as used herein, refers to cytotoxicity caused by expanded CAG-RNA. Expanded CAG-RNA mediated toxicity can result in nucleolar stress and cell death. Expanded CAG-RNA mediated toxicity can be inferred by detecting or measuring one or more of (i) rRNA upstream control element hypermethylation, (ii) a decrease in rRNA transcription, (iii) a decrease in binding of NCL to the rRNA locus, (iv) an increase in binding between ribosomal proteins and MDM2, (v) stabilization of p53, (vi) accumulation of p53 in the mitochondria, (vii) release of Bcl-xL from Bak, (viii) release of cytochrome c from the mitochondria, (ix) caspase activation, (x) and apoptosis.

The term "PolyQ-mediated cytotoxicity" "PolyQ-mediated toxicity" and the like, as used herein, refers to cytotoxicity caused by polypeptides that contain polyglutamine amino acid sequences. PolyQ-mediated cytotoxicity can result in cellular stress, endoplasmic reticulum stress, an unfolded protein response, and cell death. PolyQ-mediated cytotoxicity can be inferred by detecting or measuring one or more of (i) GRP78/BiP upregulation, (ii) caspase activation, (iii) and apoptosis. PolyQ-mediated cytotoxicity can be observed independently of expanded CAG-RNA mediated cytotoxicity by measuring GRP78/BiP upregulation as explained herein. Similarly, expanded CAG-RNA mediated cytotoxicity can be observed independently of polyQ-mediated cytotoxicity by measuring one or more of rRNA hypermethylation, NCL binding to rRNA locus, the level of rRNA expression, and binding between ribosomal proteins and MDM2 as explained herein.

RNA that contains CAG triplet nucleotide repeats can cause expanded CAG-RNA mediated cytotoxicity and polyQ-mediated cytotoxicity when the CAG repeats are translated. In some cases, the CAG repeats are not in a translated region and the expanded CAG-RNA can cause expanded CAG-RNA mediated cytotoxicity but not polyQ-mediated cytotoxicity. Similarly, if a polyglutamine polypeptide is encoded by an mRNA that does not contain CAG triplet nucleotide repeats, it can cause polyQ-mediated cytotoxicity but not expanded CAG-RNA mediated cytotoxicity. For example, a polyglutamine polypeptide can be encoded by CAG/A repeats (alternating CAG and CAA, which both encode glutamine), CAA/G repeats (alternating CAA and CAG), CAA repeats, or a combination thereof. Cells that contain expanded CAG-RNA or polyQ polypeptides can be detected by detecting expanded CAG-RNA or polyQ peptide directly, or by detecting or measuring any of the hallmarks of expanded CAG-RNA toxicity or polyQ peptide toxicity.

The term a "polyQ disease" as used herein, refers to a disease or condition that is associated with, caused by, or exacerbated by, expanded CAG-RNA and/or polyQ polypeptides. PolyQ diseases include those diseases, conditions, and symptoms that result from nucleolar stress or endoplasmic reticulum stress caused by expanded CAG-RNA, polyQ polypeptides, or both. As such, polyQ disease can be observed in cells by detecting or measuring any of the hallmarks of expanded CAG-RNA mediated cytotoxicity or polyQ-mediated cytotoxicity. Additionally, polyQ disease can be observed in cells by detecting the presence of expanded CAG-RNA or polyQ polypeptides. Furthermore, cells from or within patients suffering from polyQ disease can exhibit polyQ disease. In some cases, cells from or within subjects in which polyQ disease is suspected, e.g., due to hereditary patterns, can exhibit polyQ disease. Exemplary embodiments of polyQ diseases include, but are not limited to Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, and Spinocerebellar ataxia Type 17.

The term a "consisting essentially of" as used herein in the context of a composition containing a polynucleotide or polypeptide, can refer to a composition that does not contain other compounds that have the same biological activity. For example, a composition consisting essentially of a peptide fragment of the naturally occurring sequence of nucleolin (or such a polypeptide with 1, 2, 3, or 4 insertion, substitutions, or deletions) would not contain other inhibitors of CAG-RNA mediated cytotoxicity.

III. Compositions

A. Inhibitors of $(CAG)_n$-Mediated Toxicity

In some embodiments, compositions are provided that reduce $(CAG)_n$-mediated toxicity in a cell. Reduction of $(CAG)_n$-mediated toxicity can, in some cases, restore rRNA transcription in expanded CAG RNA-expressing cells. For example, synthetic peptides are provided that can bind to or sequester toxic RNA species. In some cases, the synthetic peptides are derived from full-length nucleolin (NCL). For example, the synthetic peptides may be derived from an RNA recognition motif (RRM) of full-length nucleolin. In some cases, the synthetic peptides are derived from the RRM2 domain of NCL.

In some cases, compositions for treating $(CAG)_n$-mediated RNA toxicity in a cell include one or more of the above synthetic peptides. For example, compositions for treating $(CAG)_n$-mediated RNA toxicity in a cell can include 1, 2, 3, 4, 5, or 6 of the peptides P1-P6. In one embodiment, the composition includes peptides P3, P5, or P3 and P5.

In some cases, the peptides are conservatively substituted at one or more of 1, 2, 3, 4, 5, 6, 7, 8, 9, 10, 11, 12, 13, and 14 positions. The peptides can also be substituted with non-natural amino acids. In some cases, the peptides are truncated. Truncated peptides include peptides in which one or more amino or carboxy terminal residues are removed. In some cases, the peptides are internally deleted such that one or more amino acids that are not at the amino or carboxy terminus are removed. In some cases, the peptides can be modified by the addition of one or more amino acids at the amino or carboxy terminus. For example, a linker or purification tag can be fused to the amino or carboxy terminus. Alternatively, the peptides can be inserted into a scaffold region of a protein, polypeptide, or other molecule as described herein. A scaffold may provide enhanced stability of the peptide in the cell, and may improve binding by reducing the conformational freedom of the peptide or influencing its three-dimensional structure.

For example, one or more of the peptides can be inserted into the CDR region of an antibody scaffold. Alternatively, non-immunoglobulin protein scaffolds can be used as peptide frameworks. See, e.g., Ku et al. (*Proc. Natl. Acad. Sci. U.S.A.* 92 (14):6552-6556 (1995)) disclosing the use of cytochrome b562 as a scaffold; U.S. Pat. Nos. 6,818,418 and 7,115,396 disclosing the use of a fibronectin or fibronectin-like protein scaffolds; Beste et al. (*Proc. Natl. Acad. Sci. U.S.A.* 96 (5): 1898-1903 (1999)) disclosing a lipocalin-based scaffold; U.S. Pat. No. 5,770,380 disclosing a synthetic rigid, non-peptide organic scaffold of calixarene, attached with one or more multiple variable peptide loops used as binding sites; and Murali et al. (*Cell Mol Biol* 49 (2):209-216 (2003)) describing a methodology for reducing antibodies into smaller peptidomimetics, termed "antibody like binding peptidomimetics" (ABiP) which may also be useful as a protein scaffold.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody scaffolds can also include such compounds.

B. Production of Peptides that Inhibit $(CAG)_n$-Mediated RNA Toxicity i. General Recombinant Technology Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a nucleolin gene, a polynucleotide encoding a polypeptide comprising the expanded CAG-RNA binding domain RRM2 or a peptide derived therefrom, and synthetic oligonucleotides can be verified after cloning or subcloning using, e.g., the chain termination method for sequencing double-stranded templates of Wallace et al., *Gene* 16: 21-26 (1981).

ii. Coding Sequence for an RRM-Related Polypeptide

Polynucleotide sequences encoding nucleolin have been determined and may be obtained from a commercial supplier or recombinantly produced.

Upon acquiring a nucleic acid sequence encoding a an RNA-recognition motif or encoding a peptide that binds expanded CAG-RNA, the coding sequence can be further modified by a number of well-known techniques such as restriction endonuclease digestion, PCR, and PCR-related methods to generate coding sequences for RRM2-related polypeptides, including RRM mutants and polypeptides comprising an expanded CAG-RNA binding sequence derived from nucleolin. The polynucleotide sequence encoding a desired RRM-related polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding an RRM-related polypeptide. See, e.g., Zhang et al., *Proc. Natl. Acad. Sci. USA*, 94: 4504-4509 (1997); and Stemmer, *Nature*, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other possible methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

iii. Modification of Nucleic Acids for Preferred Codon Usage in a Host Organism

The polynucleotide sequence encoding an RRM-related polypeptide can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the RRM-related polypeptides.

iv. Chemical Synthesis of RRM-Related Polypeptides

The amino acid sequence of RNA Recognition Motifs derived from NCL has been established as one of SEQ ID NO:4-14. A polypeptide comprising an expanded CAG-RNA binding sequence thus can also be chemically synthesized using conventional peptide synthesis or other protocols well known in the art.

Polypeptides may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook*, 2nd Ed., Springer-Verlag (1993)).

B. Expression and Purification of Peptides that Inhibit (CAG)$_n$-Mediated RNA Toxicity Following verification of the coding sequence, an RRM-related polypeptide of the present invention can be produced using routine techniques in the field of recombinant genetics, relying on the polynucleotide sequences encoding the polypeptide disclosed herein.

i. Expression Systems

To obtain high level expression of a nucleic acid encoding an RRM-related polypeptide of the present invention, one typically subclones a polynucleotide encoding the polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the RRM-related polypeptide in host cells. A typical expression cassette thus contains a promoter operably linked to the nucleic acid sequence encoding the RRM-related polypeptide and signals required for efficient polyadenylation of the transcript, ribosome binding sites, and translation termination. The nucleic acid sequence encoding the RRM-related polypeptide is typically linked to a cleavable signal peptide sequence to promote secretion of the polypeptide by the transformed cell. Such signal peptides include, among others, the signal peptides from tissue plasminogen activator, insulin, and neuron growth factor. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the RRM-related polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., an RRM-related polypeptide of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

ii. Transfection Methods

Standard transfection methods are used to produce bacterial, mammalian, yeast, insect, or plant cell lines that express large quantities of RRM-related polypeptides, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the RRM-related polypeptide.

iii. Purification of Recombinantly Produced RRM-Related Polypeptides

Once the expression of a recombinant RRM-related polypeptide in transfected host cells is confirmed, e.g., via an immunoassay such as Western blotting assay, the host cells are then cultured in an appropriate scale for the purpose of purifying the recombinant polypeptide.

1. Purification of Recombinantly Produced Polypeptides from Bacteria

When the RRM-related polypeptides of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., an RRM-related polypeptide, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide of the present invention, e.g., an expanded CAG-RNA binding sequence, is expressed in host cells in a soluble form, its purification can follow the standard protein purification procedure described below. This standard purification procedure is also suitable for purifying RRM-related polypeptides obtained from chemical synthesis.

a. Solubility Fractionation

Often as an initial step, and if the protein mixture is complex, an initial salt fractionation can separate many of the unwanted host cell proteins (or proteins derived from the cell culture media) from the recombinant protein of interest, e.g., an RRM-related polypeptide of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

b. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., an RRM-related polypeptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

c. Column Chromatography

The proteins of interest (such as an RRM-related polypeptide of the present invention) can also be separated from other proteins on the basis of their size, net surface charge, hydrophobicity, or affinity for ligands. In addition, antibodies raised against a segment of nucleolin such as an RNA recognition motif can be conjugated to column matrices and the RRM-related polypeptide immunopurified. All of these methods are well known in the art.

It will be apparent to one of skill that chromatographic techniques can be performed at any scale and using equipment from many different manufacturers (e.g., Pharmacia Biotech).

C. Inhibitors of Polyglutamine (PolyQ)-Mediated Toxicity

The present invention also provides inhibitors of polyQ mediated cytotoxicity. Such inhibitors include the peptide QBP1 (SEQ ID NO:15: S N W K W W P G I F D) or homologs (80%, 85%, 90%, 95%, or higher sequence homology) thereof that are capable of binding polyglutamine. This core amino acid sequence may contain some variations such as amino acid deletion, addition, or substitution, but should maintain an affinity to polyglutamine. As described above, such a peptide may also be incorporated into a scaffold such as an antibody scaffold, a lipocalin scaffold, a calixarene scaffold, etc.

IV. Methods

A. Identification of Compounds that Inhibit $(CAG)_n$-Mediated RNA Toxicity

An in vitro assay can be used to detect binding between nucleolin and expanded CAG-RNA or detect the binding between an RRM-related peptide and expanded CAG-RNA and to identify compounds that are capable of inhibiting nucleolin: expanded CAG-RNA binding. Such an assay can be performed in the presence of nucleolin or a peptide derived therefrom, such as any one of SEQ ID NOs: 1-14, and an expanded CAG-RNA, under conditions permitting binding. For convenience, one of the binding partners may be immobilized onto a solid support and/or labeled with a detectable moiety. A third molecule, such as an antibody (which may include a detectable label) to one of the binding partners, can also be used to facilitate detection.

In one embodiment, the expanded CAG-RNA can be labeled with a fluorophore and its intrinsic fluorescence anisotropy due to tumbling in solution can be measured. If a fluorescent molecule is excited with polarized light then the emission will also be polarized. The extent of polarization of the emission is usually described in terms of anisotropy (r). As molecules are tumbling in solution, the emitted light is then depolarized. The depolarization of the fluorescent molecule is dependent on the size and shape of the rotating molecule and also the viscosity of the solution. The smaller the molecule, the more rapidly it rotates and the more the light is depolarized and hence the lower the anisotropy. If a larger molecule interacts with the fluorescent molecule the rotation of the complex will be slower than of the unbound molecules and result in an increase in the fluorescence anisotropy. Inhibitors can be identified by incubating the complex in the presence of a test compound and measuring a reduction in fluorescence anisotropy as compared to a control in which the test compound is not added to the complex.

In some cases, the binding assays can be performed in a cell-free environment; whereas in other cases, the binding assays can be performed in a cell, frequently using cells recombinantly or endogenously expressing an appropriate expanded CAG-RNA molecule. For example, cells expressing an expanded CAG-RNA molecule can be contacted with a test compound and one or more markers of nucleolar stress can be assayed. Such markers include rRNA transcription, rRNA UCE hypermethylation, p53 stability, and apoptosis (e.g., as shown by a decrease in rhabdomeres per ommatidium in the eye of a fruit fly).

To screen for compounds capable of inhibiting nucleolin: expanded CAG-RNA binding, the above-described assays can be performed both in the presence and absence of a test compound, and the level of nucleolin: expanded CAG-RNA binding compared. If nucleolin: expanded CAG-RNA binding is suppressed in the presence of the test compound, for example, at a level of at least 10%, more preferably at least 20%, 30%, 40%, or 50%, or even higher, the test compound is then deemed an inhibitor nucleolin: expanded CAG-RNA binding and may be subject to further testing to confirm its ability to inhibit nucleolar stress.

In some cases, an inhibitor could be identified by detecting an increase in rRNA transcription relative to a control cell expressing an expanded CAG-RNA molecule that is not contacted with the test compound. As another example, an inhibitor could be identified by detecting a decrease in methylation of the rRNA UCE relative to a control cell expressing an expanded CAG-RNA molecule that is not contacted with the test compound. As yet another example, an inhibitor could be identified by detecting a decrease in p53 stabilization (e.g., a reduction in p53 accumulation) relative to a control cell expressing an expanded CAG-RNA molecule that is not contacted with the test compound. As yet another example, an inhibitor could be identified by detecting an increase in the number of rhabdomeres per ommatidium in the eye of a fruit fly relative to a control eye in which the cells express an expanded CAG-RNA molecule that is not contacted with the test compound. More details and some examples of such binding assays can be found in the Examples section of this application.

A binding assay is also useful for confirming that a polypeptide comprising an expanded CAG-RNA binding sequence can indeed specifically bind expanded CAG-RNA. For instance, a polypeptide comprising any one of SEQ ID NOs:1-14 but not the full length NCL sequence can be recombinantly expressed, purified, and placed in a binding assay with expanded CAG-RNA, or expanded CAA/G-RNA, in which every alternate guanine nucleotide is substituted with adenine as a negative control. If deemed to have sufficient expanded CAG-RNA binding ability and specificity, the polypeptide sequence can then be used as a positive control for identifying inhibitors of NCL: expanded CAG-RNA binding. Similarly, a polypeptide comprising a core sequence with a high level of homology (e.g., 90%, 95% or higher) to any one of SEQ ID NOs: 1-14 can be tested and, if appropriate, can be used as a positive control for identifying inhibitors of NCL: expanded CAG-RNA binding.

Inhibitors of NCL: expanded CAG-RNA binding can have diverse chemical and structural features. For instance, an inhibitor can be a non-functional NCL mutant that retains expanded CAG-RNA binding ability, an antibody that interferes with NCL: expanded CAG-RNA binding, or any small molecule or macromolecule that simply hinders the interaction between NCL and expanded CAG-RNA. Essentially any chemical compound can be tested as a potential inhibitor of NCL: expanded CAG-RNA binding. Most preferred are generally compounds that can be dissolved in aqueous or organic (especially DMSO-based) solutions. Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer.*

Chem. Soc. 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539, 083), antibody libraries (see, e.g., Vaughn et al., *Nature Biotechnology*, 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525, 735 and 5,519,134; morpholino compounds, U.S. Pat. No. 5,506,337; and benzodiazepines, U.S. Pat. No. 5,288,514).

B. Identification of Compounds that Inhibit Polyglutamine-Mediated Toxicity

The triplet nucleotide CAG encodes for glutamine. Therefore, in general, diseases which exhibit expanded CAG-RNA mediated cytotoxicity also exhibit polyglutamine (polyQ)-mediated cytotoxicity. However polyQ-mediated cytotoxicity can be differentiated from expanded CAG-RNA mediated cytotoxicity in an appropriate assay.

For example, a cell can be transfected with an expression construct encoding for an expanded CAG-RNA that is not translated. In some cases, the CAG-RNA portion is not translated, while other portions of the expression construct are translated. For example, the present invention provides a $DsRed_{CAGn}$ expression cassette in which n can from about 20 to about 100, including 20, 30, 40, 50, 60, 70, 78, 80, 90, or 100. In the $DsRed_{CAGn}$ expression cassette, the expanded CAG-RNA is present in the 3' UTR of the mRNA encoded by the expression cassette. Thus, in a cell transfected with the expression cassette, the DsRed protein is translated and fluorescence can be detected to indicate successful transformation of the cell, but only CAG-RNA mediated cytotoxicity is exhibited. In this model, the length of the CAG expansion will generally correlate with increased CAG-RNA mediated cytotoxicity. For example, $DsRed_{CAG0}$ exhibits no discernible CAG-RNA mediated cytotoxicity, while $DsRed_{CAG100}$ exhibits a high level of CAG-RNA mediated cytotoxicity.

Conversely, a cell can be transfected with an expression cassette that encodes for a protein containing a polyQ sequence. If the cassette encodes the polyQ sequence by encoding an expanded CAG-RNA, then the cell will exhibit both CAG-RNA mediated cytotoxicity and polyQ cytotoxicity. However, if the construct encodes the polyQ sequence using CAA, CAG/A, or CAA/G (alternating CAA and CAG), then a transfected cell will exhibit polyQ cytotoxicity but not CAG-RNA mediated cytotoxicity. Such a cell can be identified because it will not exhibit hypermethylation of the UCE of the rRNA gene, or will not exhibit a reduction in rRNA transcription. However, the cell can exhibit markers of polyQ-mediated stress such as an increase in expression of a marker associated with polyQ-mediated stress.

GRP78/BiP is a marker that is specific for polyQ-mediated cytotoxicity as demonstrated by its upregulation in cells transfected with an expression construct encoding the $MJD_{CAA/G78}$ peptide and its lack of upregulation in cells transfected with the $DsRed_{CAG78}$ construct in which the $CAG_{78}$ (SEQ ID NO:18) triplet nucleotide repeat is in the 3' UTR. Similarly, polyQ peptide aggregation is specific for polyQ-mediated cytotoxicity. In contrast, rRNA transcription and hypermethylation of the UCE of the rRNA gene are markers that are specific for expanded CAG-RNA mediated cytotoxicity because rRNA transcription is reduced and hypermethylation is exhibited in cells transfected with the $DsRed_{CAG78}$ construct in which the $CAG_{78}$ (SEQ ID NO:18) triplet nucleotide repeat is in the 3' UTR but not in cells transfected with an expression construct encoding the $MJD_{CAA/G78}$ peptide. Therefore, expanded CAG-RNA and polyQ protein cytotoxicity can be independently monitored by measuring expression levels of rRNA and GRP78/BiP respectively in cells. In some cases, expanded CAG-RNA mediated cytotoxicity can be specifically monitored by detecting hypermethylation of the UCE of the rRNA gene or rRNA transcription and polyQ-mediated cytotoxicity can be specifically monitored by measuring expression of GRP78/BiP or aggregation of the polyQ peptide.

In one embodiment, a cell is transfected with a construct that causes polyQ mediated cytotoxicity but not expanded CAG-RNA mediated cytotoxicity, and contacted with a test compound. The cell can then be assayed for a reduction in polyQ mediated cytotoxicity. In another embodiment, a cell is transfected with a construct that causes polyQ mediated cytotoxicity and expanded CAG-RNA mediated cytotoxicity and contacted with a test compound. The cell can then be assayed for a reduction in polyQ mediated cytotoxicity, expanded CAG-RNA mediated cytotoxicity, or both. In this manner compounds that reduce expanded CAG-RNA mediated cytotoxicity, reduce polyQ-mediated cytotoxicity, or reduce both can be identified. Test compounds include peptide and small molecule chemical libraries as described above. Test compounds also include the QBP1 peptide, SEQ ID NO: 15, or a derivative thereof. QBP1 peptide, SEQ ID NO: 15, or a derivative thereof can also be used as a positive control.

C. Methods of Treatment of PolyQ Disease

Provided herein are methods for treating polyQ disease in a cell that contains an RNA containing a $(CAG)_n$ triplet nucleotide repeat. Such methods include contacting the cell with an effective amount of a composition that reduces expanded-CAG RNA-mediated cytotoxicity. Methods of contacting can be performed in vitro and in vivo. In some cases, the RNA containing the $(CAG)_n$ triplet nucleotide repeat contains at least 10, 20, 30, 40, 50, 60, 70, 78, or 100 CAG (SEQ ID NO:16) triplet nucleotides. Such a cell is likely to exhibit nucleolar stress. In some cases, the composition itself binds the RNA containing the $(CAG)_n$ triplet nucleotide repeat. Such binding activity can act to sequester the RNA containing a $(CAG)_n$ triplet nucleotide repeat from disrupting cellular processes. For example, the composition can sequester the RNA containing a $(CAG)_n$ triplet nucleotide repeat from binding to nucleolin. In some cases, the cell expresses a nucleic acid encoding $MJD_{CAGn}$, or $DsRed_{CAGn}$, wherein each n is independently selected from about 10, 20, 30, 40, 50, 60, 70, 78, and 100. In some cases, the cell is from, or in, a subject suffering from Huntington's Disease, Dentatorubro-pallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17.

Methods for treating a polyQ disease also include contacting a cell that expresses a peptide containing a polyQ amino acid sequence include the steps of contacting the cell with an effective amount of a composition that reduces polyQ-mediated cytotoxicity. In some cases, the composition itself binds the peptide containing the polyQ sequence. Such binding activity can act to sequester the polyQ peptide from disrupting cellular processes. For example, the composition can sequester the polyQ peptide from forming intracellular aggregates. In some cases, the cell expresses a nucleic acid encoding $MJD_{CAGn}$, $MJD_{CAA/Gn}$, or $MJD_{CAG/An}$, wherein each n is independently selected from about 10, 20, 30, 40, 50, 60, 70, 78, and 100. In some cases, the cell is from, or in, a subject suffering from Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17.

V. Pharmaceutical Compositions and Administration

The present invention also provides pharmaceutical compositions or physiological compositions comprising an effective amount of a compound that inhibits expanded CAG-RNA mediated cytotoxicity, inhibits polyQ-mediated cytotoxicity, inhibits both forms of cytotoxicity, or a mixture of a compound that inhibits CAG-RNA mediated cytotoxicity and a compound that inhibits polyQ-mediated cytotoxicity. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal. Routes of administering the pharmaceutical compositions include local delivery to an organ or tissue suffering from a condition exacerbated by expanded CAG-RNA mediated cytotoxicity, polyQ-mediated cytotoxicity, or both forms of cytotoxicity (e.g., injection to the affected tissue) at daily doses of about 0.01-5000 mg, preferably 5-500 mg, of a compound of the present invention for a 70 kg adult human per day. The appropriate dose may be administered in a single daily dose or as divided doses presented at appropriate intervals, for example as two, three, four, or more subdoses per day.

For preparing pharmaceutical compositions containing a compound of the present invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., a polypeptide that binds expanded CAG-RNA or a polypeptide that binds polyQ containing peptides, or a mixture of a polypeptide that binds expanded CAG-RNA and a polypeptide that bind polyQ containing peptides. In tablets, the active ingredient (an inhibitor of expanded CAG-RNA mediated cytotoxicity, an inhibitor of polyQ-mediated cytotoxicity, a compound that inhibits both forms of cytotoxicity, or a mixture of compounds that inhibits both forms of cytotoxicity) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of an inhibitor of expanded CAG-RNA mediated cytotoxicity, an inhibitor of polyQ-mediated cytotoxicity, a compound that inhibits both forms of cytotoxicity, or a mixture of compounds that inhibits both forms of cytotoxicity. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of an inhibitor of the present invention with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an inhibitor of expanded CAG-RNA mediated cytotoxicity, an inhibitor of polyQ-mediated cytotoxicity, a compound that inhibits both forms of cytotoxicity, or a mixture of compounds that inhibits both forms of cytotoxicity) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an inhibitor of expanded CAG-RNA mediated cytotoxicity, an inhibitor of polyQ-mediated cytotoxicity, a compound that inhibits both forms of cytotoxicity, or a mixture of compounds that inhibits both forms of cytotoxicity) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing an inhibitor of CAG-RNA mediated cytotoxicity, an inhibitor of polyQ-mediated cytotoxicity or a mixture of an inhibitor of CAG-RNA mediated cytotoxicity and an inhibitor of polyQ-mediated cytotoxicity can be administered for prophylactic and/or therapeutic treatments. In therapeutic applications, compositions are administered to a patient already suffering from a condition that may be exacerbated by the expression of expanded CAG-RNA or expression of polyQ peptides in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the inhibitor per day for a 70 kg patient, with dosages of from about 5 mg to about 500 mg of the inhibitor per day for a 70 kg patient being more commonly used.

In prophylactic applications, pharmaceutical compositions containing an inhibitor of CAG-RNA mediated cytotoxicity, an inhibitor of polyQ-mediated cytotoxicity or a mixture of an inhibitor of CAG-RNA mediated cytotoxicity and an inhibitor of polyQ-mediated cytotoxicity are administered to a patient susceptible to or otherwise at risk of developing a disease or condition in which expression of expanded CAG-RNA or expression of polyQ peptides is undesirable, in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,000 mg of the inhibitor for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should effectively inhibit hypermethylation of the UCE of the rRNA gene, nucleolar stress, downregulation of rRNA transcription, polyQ peptide aggregation, GRP78/BiP overexpression or expanded CAG-RNA mediated or polyQ peptide mediated cell death in the patient, either therapeutically or prophylactically.

VI. Therapeutic Applications Using Nucleic Acids

A variety of diseases can be treated by therapeutic approaches that involve introducing a nucleic acid encoding a polypeptide inhibitor of CAG-RNA mediated cytotoxicity, a polypeptide inhibitor of polyQ-mediated cytotoxicity or a mixture of a polypeptide inhibitor of CAG-RNA mediated cytotoxicity and a polypeptide inhibitor of polyQ-mediated cytotoxicity into a cell such that the coding sequence is transcribed and the polypeptide inhibitor(s) are produced in the cell. Diseases amenable to treatment by this approach include Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17. For discussions on the application of gene therapy towards the treatment of genetic as well as acquired diseases, see, Miller *Nature* 357:455-460 (1992); and Mulligan *Science* 260:926-932 (1993).

A. Vectors for Gene Delivery

For delivery to a cell or organism, a polynucleotide encoding a polypeptide that inhibits CAG-RNA mediated cytotoxicity, a polypeptide that inhibits polyQ-mediated cytotoxicity or polynucleotide encoding both a polypeptide inhibitor of CAG-RNA mediated cytotoxicity and a polypeptide inhibitor of polyQ-mediated cytotoxicity can be incorporated into a vector. Examples of vectors used for such purposes include expression plasmids capable of directing the expression of the nucleic acids in the target cell. In other instances, the vector is a viral vector system wherein the polynucleotide is incorporated into a viral genome that is capable of transfecting the target cell. In a preferred embodiment, the polynucleotide encoding a polypeptide inhibitor can be operably linked to expression and control sequences that can direct expression of the polypeptide in the desired target host cells. Thus, one can achieve expression of the polypeptide inhibitor under appropriate conditions in the target cell.

B. Gene Delivery Systems

Viral vector systems useful in the expression of a polypeptide inhibitor of the present invention include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the genes of interest (e.g., one encoding for a polypeptide inhibitor of the present invention) are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors may also be useful for introducing the coding sequence of a polypeptide inhibitor of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.*, 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405, 712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA*, 81:6349-6353 (1984); Danos and Mulligan *Proceedings of the National Academy of Sciences, USA*, 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

C. Pharmaceutical Formulations

When used for pharmaceutical purposes, the nucleic acid encoding a polypeptide inhibitor of the present invention is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences*, Mack Publishing Company, Philadelphia, Pa., 17th ed. (1985).

D. Administration of Formulations

The formulations containing a nucleic acid encoding a polypeptide inhibitor of the present invention can be delivered to any tissue or organ using any delivery method known to the ordinarily skilled artisan. In some embodiments of the invention, the nucleic acids encoding the inhibitor polypeptides are formulated for subcutaneous, intramuscular, intravenous, intraperitoneal, or intratumor injection.

The formulations containing the nucleic acid of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, ultrasound, electroporation, or biolistics. In further embodiments, the nucleic acids are taken up directly by the tissue of interest.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6): 2414-9 (1996); Koc et al., *Seminars in Oncology* 23(1):46-65 (1996); Raper et al., *Annals of Surgery* 223(2):116-26 (1996); Dalesandro et al., *J. Thorac. Cardi. Surg.*, 11(2):416-22 (1996); and Makarov et al., *Proc. Natl. Acad. Sci. USA* 93(1): 402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses ranging from about 10 ng-1 g, 100 ng-100 mg, 1 µg-10 mg, or 30-300 µg DNA per patient are typical. Doses generally range between about 0.01 and about 50 mg per kilogram of body weight, preferably between about 0.1 and about 5 mg/kg of body weight or about $10^8$-$10^{10}$ or $10^{12}$ particles per injection. In general, the dose equivalent of a naked nucleic acid from a vector is from about 1 µg-100 µg for a typical 70 kg patient, and doses of vectors which include a retroviral particle are calculated to yield an equivalent amount of nucleic acid encoding a polypeptide that inhibits expanded CAG-RNA mediated cytotoxicity or a polypeptide that inhibits polyQ mediated cytotoxicity, or a nucleic acid that encodes a polypeptide that inhibits CAG-RNA mediated cytotoxicity and a polypeptide that inhibits polyQ mediated cytotoxicity.

VII. Kits

The invention also provides kits for inhibiting expanded CAG-RNA mediated cytotoxicity, inhibiting polyQ mediated cytotoxicity, or inhibits both expanded CAG-RNA mediated cytotoxicity and polyQ mediated cytotoxicity according to the methods of the present invention. The kits typically include a container that contains a pharmaceutical composition having an effective amount of an inhibitor of the present invention as well as informational material containing instructions on how to dispense the pharmaceutical composition, including a description of the type of patients who may be treated, e.g., a patient suffering from Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17. In some case, the kit can contain instructions regarding the dosage schedule (e.g., dose amount and frequency) and route of administration.

EXAMPLES

The following examples are provided by way of illustration only and not by way of limitation. Those of skill in the art will readily recognize a variety of non-critical parameters that could be changed or modified to yield essentially the same or similar results.

Example 1

Endogenous NCL Interacts with Expanded CAG RNAs

Cells expressing were $MJD_{CAG27}$, $MJD_{CAG78}$, and $MJD_{CAA/G78}$ RNAs were suspended in 200 µL lysis buffer (20 mM Hepes, pH 7.4, 150 mM NaCl, 5 mM MgCl2, and 0.5% Nonidet P-40), and 10% of the lysate was saved as input control while the remaining lysate was subjected to immunoprecipitation using the anti-nucleolin antibody 3G4B2 (Millipore; 1:200) at 4° C. overnight in the presence of protein A agarose beads. After incubation, the beads were washed in lysis buffer three times each for 10 min. To elute proteins, agarose beads were boiled in 30 µL of 2×SDS sample buffer at 99° C. for 10 min. Each experiment was repeated at least three times and comparable results were obtained. The results show that endogenous NCL interacts specifically with $MJD_{CAG78}$RNA, but not with the unexpanded CAG and discontinuous expanded CAG control RNAs (FIG. 1A).

Example 2

GST-NCL Interacts with Expanded CAG RNAs

Purified GST-nucleolin (GST-NCL) protein was purchased from Abnova (H00004691-P01), and the control GST protein was expressed and purified as previously described (Tsoi H, et al. 2011). The $CAG_{78}$ (SEQ ID NO:18) and $CUG_{78}$ (SEQ ID NOP:19) RNAs were synthesized from a pcDNA3.1-$MJD_{CAG78}$ PCR product, using the MEGAscript kit (Ambion) with the following primer pairs: T7CAGF, 5'-TAA AC GAC TCA CTA TAG GGA GAA GAA GCC TAC TTT GAA AAA-3' (SEQ ID NO:20) and CAGR, 5'-CTG TCC TGA TAG GTC CCG-3' (SEQ ID NO:21) for $CAG_{78}$ (SEQ ID NO:18); and T7CUGF, 5'-TAA TAC GAC TCA CTA TAG GGA GAA GAC ACG ACT ATC CAG GGC-3' (SEQ ID NO:22) and CUGR, 5'-CTT CGG ATG AAA CTT TTT-3' (SEQ ID NO:23) for $CUG_{78}$ (SEQ ID NO:19). To perform in vitro protein-RNA interaction, 50 ng of GST protein was first captured by glutathione Sepharose beads (GE Healthcare). The purified in vitro transcribed RNA (10 pmol) was allowed to bind with GST-coated glutathione Sepharose beads and the mixture was incubated at 4° C. overnight in a 500-µL reaction volume. Before elution, the protein-RNA mixture was washed three times with 1 mL of binding buffer [20 mM Hepes, pH 7.4, 150 mM NaCl, 5 mM MgCl2, 0.5% Nonidet P-40, 40 units RNAsin (Promega), and 1 mg/mL yeast tRNA (Sigma)]. Bound RNA was then extracted for RT-PCR as described in Tsoi H, et al. 2011. Each experiment was repeated at least three times and comparable results were obtained. The results show that GST-NCL interacted with $CAG_{78}$ (SEQ ID NO:18) but not with $CUG_{78}$ (SEQ ID NOP:19) RNA and thus NCL interacts directly and specifically with expanded CAG RNAs (FIG. 1B).

Example 3

Synthetic NCL Peptides Disrupt NCL: Expanded CAG-RNA Interaction

Since it was demonstrated that NCL is involved in a direct physical interaction with expanded CAG-RNA, and the protein structure of NCL RRM2 has been solved (PDB ID: 1FJC), several peptides (P1-P6) were designed (SEQ ID NOs: 4-9, P1-P6) based on the structural information of the RRM2 and the predicted structure of RRM3. These peptides were then tested for the ability to interact with expanded CAG RNA. A competition assay was first performed to determine whether any of the peptides could disrupt the interaction between purified NCL and expanded CAG RNA. Ten µM of each peptide was incubated with purified GST-NCL and $CAG_{78}$ (SEQ ID NO:18) RNA. Purified GST-NCL protein and in vitro transcribed RNAs ($CAG_{78}$ (SEQ ID NO:18) and $CUG_{78}$ (SEQ ID NO:19)) were used in the binding reactions. Non-fusion GST protein was used as a negative control. The NCL: CAG78 RNA complex was precipitated as described above using glutathione beads. Bound RNA was then extracted for RT-PCR as described above. Peptide 3 (P3) derived from RRM2 and peptide 5 (P5) derived from RRM3 were able to interfere with the interaction between purified NCL and expanded CAG RNA (FIG. 1C). Since P3 was derived from the NCL RRM2 domain whose structure had been solved by empirical means, it was thus chosen for further investigation.

Example 4

Synthetic NCL Peptide P3 Disrupts NCL: Expanded CAG-RNA Interaction in a Dose Dependent Manner A similar competition assay was performed with peptide P3 incubated at various doses to determine whether the interaction between purified NCL and expanded CAG RNA was disrupted in a dose dependent manner. The P3 peptide was incubated at 10, 50, 100, 250, and 750 μM with NCL and $CAG_{78}$ (SEQ ID NO:18) RNA. Purified GST-NCL protein and in vitro transcribed RNAs ($CAG_{78}$ (SEQ ID NO:18) and $CUG_{78}$ (SEQ ID NOP:19)) were used in the binding reactions. Non-fusion GST protein was used as a negative control. The NCL:$CAG_{78}$ RNA complex was precipitated as described above using glutathione beads. Bound RNA was then extracted for RT-PCR as described above. We found peptide 3 (P3) derived from RRM2 and peptide 5 (P5) derived from RRM3 were able to interfere with the interaction between purified NCL and expanded CAG RNA (FIG. 1D).

Example 6

Overexpression of Wild-Type P3 Peptide Reduces Nucleolar Stress

Figure 2:
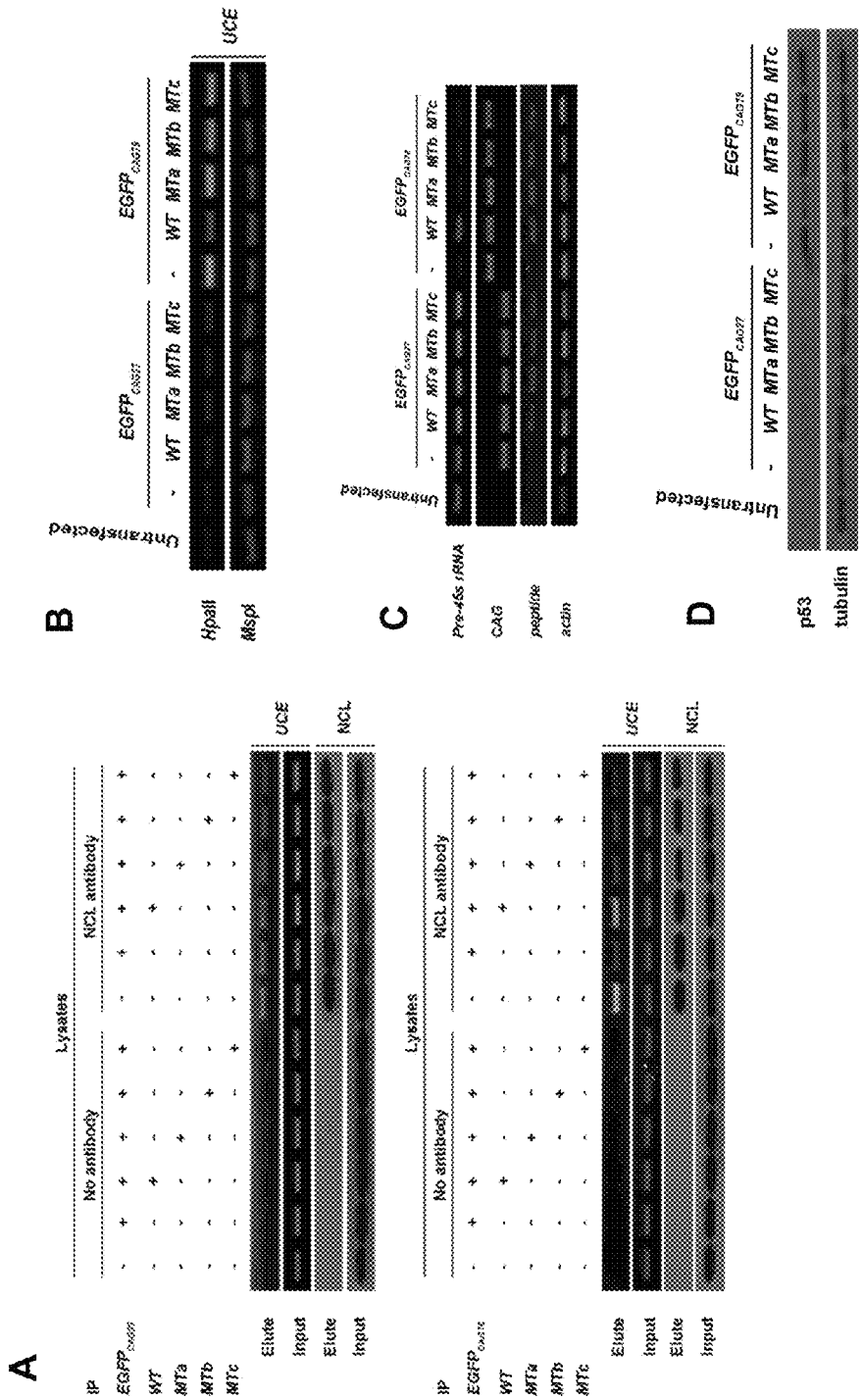
FIG. 2. Depicts the effect of transfection of wild-type (WT) and mutant (MT) NCL peptide 3 constructs on (A) endogenous NCL binding to upstream control element (UCE) of rRNA promoter, (B) UCE DNA methylation, as measured by HpaII methylation assay, (C) rRNA transcription, and (D) p53 protein stabilization in expanded CAG RNA-expressing cells. The CAG repeat sequence EGFP$_{CAG}$ is located in the 3' UTR of the expression constructs, thus only expanded CAG RNA is produced and no expanded polyglutamine protein is translated from the transcript. "-" represents EGFP$_{CAG}$ RNA-expressing cells without transfected with any NCL P3 peptide expression construct (neither WT nor MT). "Untransfected" represents cells that were not transfected with ANY expression construct. (E) Quantitative RT-PCR demonstrates that expression of P3WT in expanded CAG expressing HEK293 cells rescued rRNA transcription.
Figure 2:
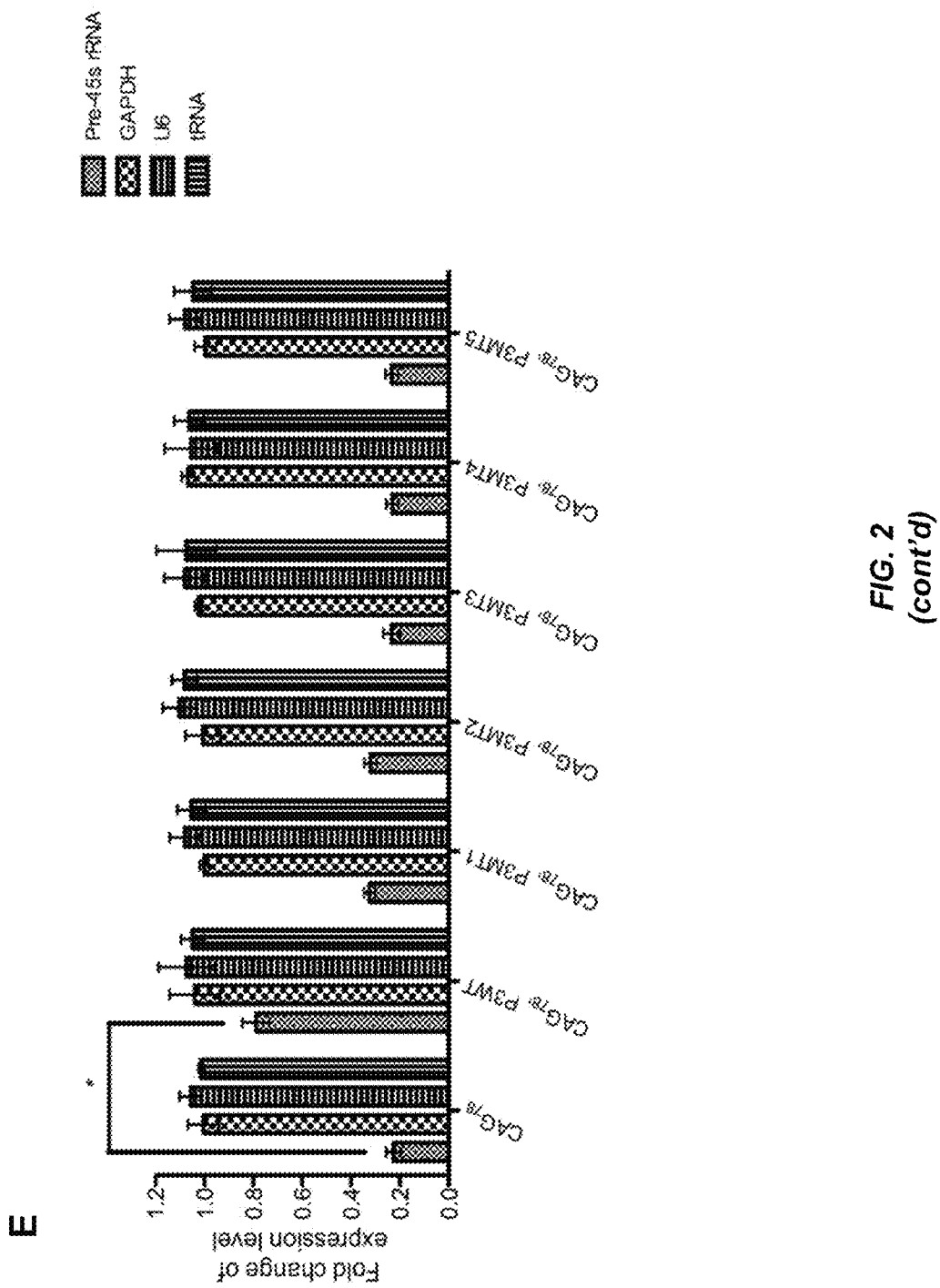

To test whether the P3 peptide is capable of counteracting expanded CAG RNA-mediated nucleolar stress induction, we generated mammalian expression constructs carrying either wild-type (WT) or mutant (MT) P3 sequences. In the three P3 mutants (MTa to MTc), a select single amino acid was mutated to alanine. The residue mutated to alanine was selected on the basis of the experimental protein crystallographic structure of NCL RRM2 (www.rcsb.org/pdb/explore/explore.do?structureId=1FJC), and all mutated residues are located in the RNA interaction surface of NCL RRM2. Cell lysates co-transfected with both P3 (WT or MT) and expanded CAG-RNA constructs were prepared and examined for the ability of P3 (WT or MT) peptide to 1) restore the binding of endogenous NCL to the UCE rRNA promoter (FIG. 2A); 2) reduce UCE hypermethylation (FIG. 2B); 3) resume transcription of the rRNA gene (FIG. 2C) and 4) prevent p53 protein accumulation in cells (FIG. 2D). Expression of the P3 (WT and MT) constructs was confirmed by RT-PCR (FIG. 2C). The effects of P3 expression in HEK293 cells under nucleolar stress was also analyzed quantitatively by RT-PCR (FIG. 2E).

For the hypermethylation assay, genomic DNA was extracted from cell lysates and digested with HpaII or MspI prior to PCR amplification. HpaII is restriction enzyme that is sensitive to CpG methylation; MspI recognizes the same cleavage sequence but is methylation-insensitive. Because of this difference, relatively more DNA template would remain intact in the HpaII-treated sample when compared with the MspI control if the genomic DNA is hypermethylated. This results in a relatively more efficient PCR amplification. Actin and tubulin were used as RNA and protein loading controls for FIGS. 2C and 2D respectively.

The CAG repeat sequence of the $EGFP_{GAG}$ constructs is located in the 3' UTR of the constructs, thus only expanded CAG-RNA would be produced and no expanded polyglutamine protein would be translated from the transcript. "-" represents $EGFP_{CAG}$ RNA-expressing cells without transfected with any NCL P3 peptide expression construct (neither WT nor MT). "Untransfected" represents cells that were not transfected with ANY expression construct.

It was found that the WT P3 construct was capable of resuming endogenous NCL/UCE interaction, reducing UCE hypermethylation, promoting rRNA transcription and reducing p53 protein accumulation (FIG. 2A-D). In contrast, the MTa-c P3 constructs did not show any rescuing effect. This suggests that the original amino acids in these three locations are essential in enabling P3 to exert its nucleolar stress-suppressing effect.

For the quantitative RT-PCR assay, DNA constructs carrying wild-type and mutant P3 mutant sequences were introduced into mammalian expression vector pcDNA3.1. The effect of different P3 mutants on nucleolar stress suppression was determined by real time-PCR analysis. The results demonstrated that expression of wild type P3 could rescue rRNA transcription (FIG. 2E). In addition, the results also showed that expression of wild type P3 did not alter gene expression mediated by RNA polymerases II and III as indicated by the expression level of GAPDH, tRNA and U6 (FIG. 2E). Therefore, the effect of P3 was specific. Based on the results, it was confirmed that P3 specifically suppresses nucleolar stress induced by expanded CAG RNA expression.

Example 7

Mutational Analysis of the P3 Peptide Nucleolar Stress Reduction Activity

To identify amino acids that are critical for P3 action, different mutants of P3 (MT1-5) were generated. Each mutant carries one or more alanine amino acid substitution. DNA constructs carrying mutant P3 mutant sequences were introduced into mammalian expression vector pcDNA3.1. Nucleolar stress suppression was determined by real time-PCR analysis. The results demonstrated that only expression of wild type P3 could resume rRNA transcription, and none of the P3 mutant retained the nucleolar stress suppression activity (FIG. 2E). In addition, the results also showed that expression of wild type P3 did not alter gene expression mediated by RNA polymerases II and III as indicated by the expression level of GAPDH, tRNA and U6 (FIG. 2E). Therefore, the effect of P3 was specific. Based on the results, it was confirmed that P3 specifically suppresses nucleolar stress induced by expanded CAG RNA expression.

Example 8

Figure 3:
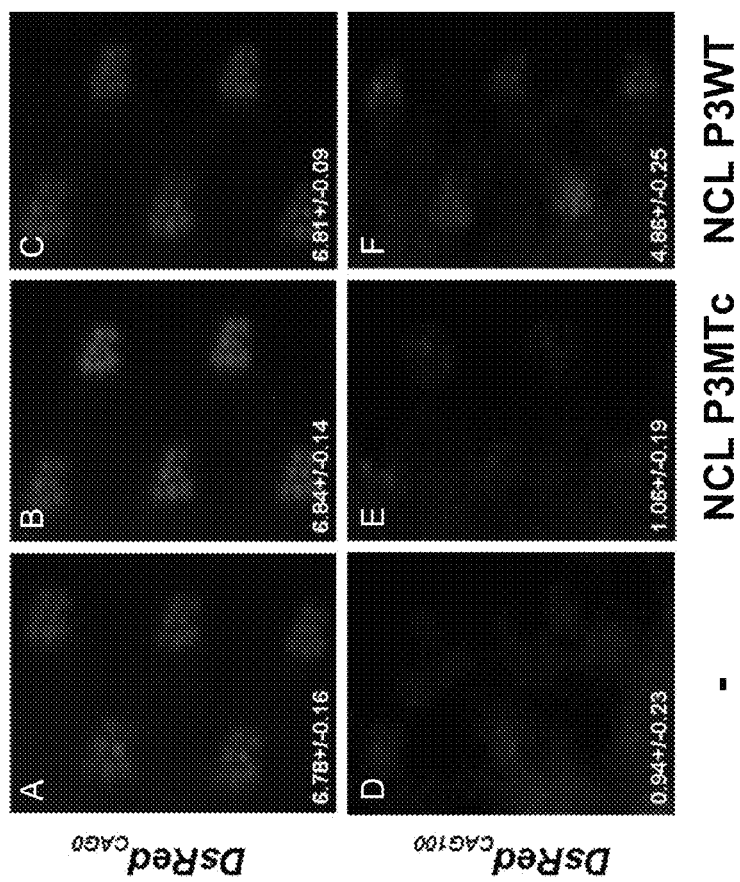
FIG. 3. Illustrates an in vivo reduction in expanded CAG-RNA toxicity by feeding Drosophila fly lines that overexpress DsRed$_{CAG100}$ RNA with synthetic Nucleolin P3 peptide. DsRed$_{CAG0}$ (A-C) and DsRed$_{CAG100}$ (D-F) F1 larvae were fed with 100 µM of NCL P3 peptide until adulthood. Representative images of rhabdomeres (light-sensing organelles in eyes) taken from 1 day-old adult flies are shown. The average number of rhabdomeres per ommatidium (single eye unit of the adult flies) is shown at the bottom left hand corner of each image, and "+/−" represents s.e.m. from 3 independent sets of experiments. "NCL P3WT" represents wildtype NCL P3 peptide while "NCL P3MTc" represents mutant c NCL P3 peptide.

NCL Exerts a Suppressive Effect on Expanded CAG-RNA Toxicity in Drosophila $DsRed_{CAG}$ RNA was expressed in Drosophila fly eyes. $DsRed_{CAG0}$ (FIGS. 3A-C) and $DsRed_{CAG100}$ (FIGS. 3D-F) using a pseudopupil assay (Chan W M, et al. 2011). F1 larvae were fed with 100 μM of NCL P3 peptides until adulthood. The overexpression caused the integrity of the internal eye structure to deteriorate, as indicated by the reduced number of rhabdomeres which are subcellular organelles responsible for phototransduction (FIG. 3D). $DsRed_{CAG100}$ larvae were fed with synthetic P3MTc (FIG. 3E) or P3 (FIG. 3F) peptide at 100 μM. A satisfactory suppression of $DsRed_{CAG100}$ RNA toxicity was observed as indicated by the rise of pseudopupil assay score (FIG. 3F). Similar to the cell data, NCL P3MTc mutant peptide did not exert any rescuing effect when administered to $DsRed_{CAG100}$ flies (FIG. 3E). Further, no dominant internal eye deterioration was observed when the non-toxic control flies $DsRed_{CAG0}$ were fed with the same concentration of P3 peptide (FIG. 3C). This result indicates that the synthetic P3 peptide administered at this concentration did not exert any dominant toxic effect on neurons in vivo.

Figure 4:
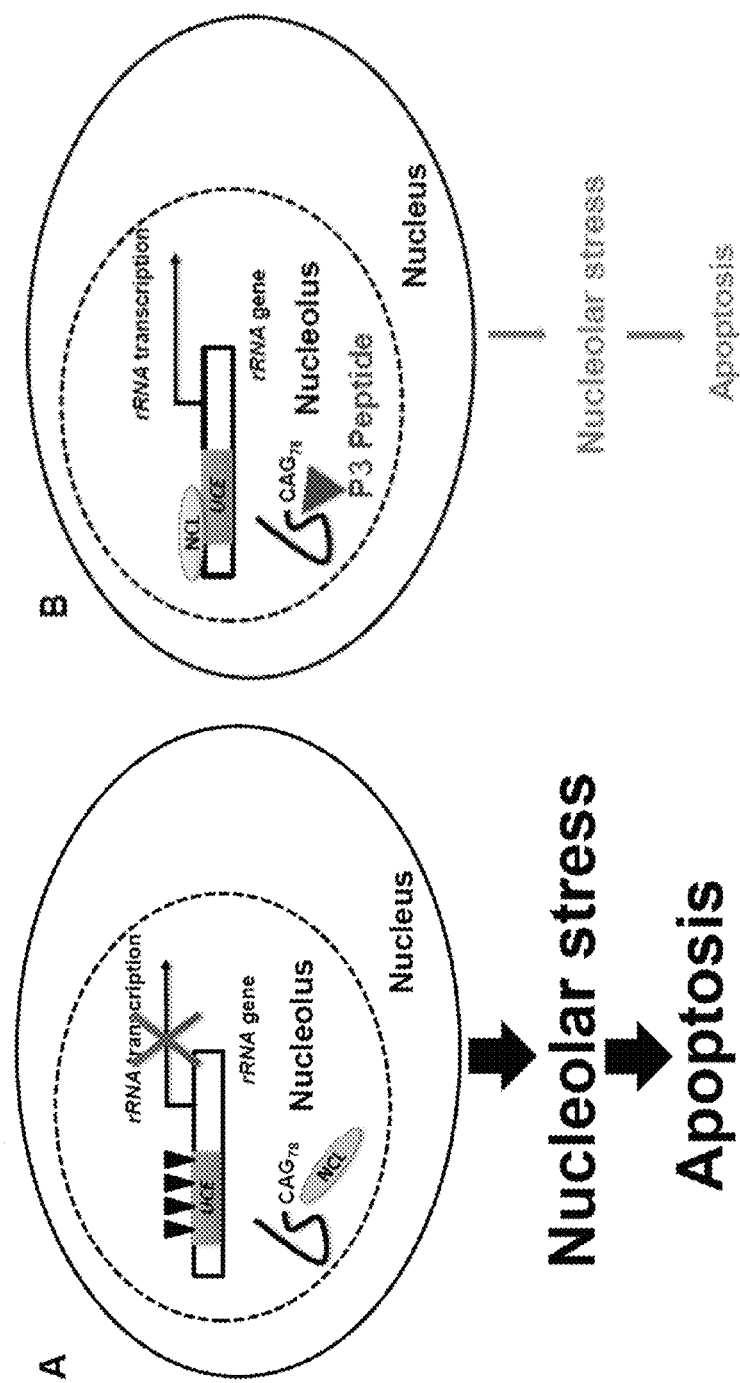
FIG. 4. Depicts a proposed mechanism of action of synthetic nucleolin peptide 3 in reducing nucleolar stress induction. (A) Expanded CAG RNA (shown as CAG$_{78}$ (SEQ ID NO:18) in this figure) interacts with Nucleolin (NCL). This interaction prevents NCL from binding to upstream control element (UCE) of rRNA promoter. This consequently leads to rRNA promoter hypermethylation and downregulation of rRNA transcription. Eventually, this causes apoptosis via nucleolar stress induction (Tsoi et al., 2012). (B) The specific binding of NCL P3 peptide (red triangle) with expanded CAG RNA allows endogenous NCL protein to interact with UCE. This prevents UCE from being hypermethylated and thus mitigates rRNA transcription dysregulation. As a result, nucleolar stress induction is reduced.

Based on these findings, the following mechanism of action of NCL P3 peptide in suppressing expanded CAG RNA-induced nucleolar stress is proposed (FIG. 4). The expression of expanded CAG RNA in cells recruits endogenous NCL protein and prevents it from binding to UCE of the rRNA promoter. This results in UCE hypermethylation and downregulation of rRNA transcription. Nucleolar stress is thus triggered, as is apoptosis (FIG. 4A). The novel synthetic NCL P3 peptide interacts with expanded CAG RNA, which thus frees up endogenous NCL protein to interact with UCE. As a result, this prevents hypermethylation on UCE, and thus preserves rRNA transcription. Consequently, nucleolar stress triggered by expanded CAG RNAs is alleviated.

Example 9

Figure 5:
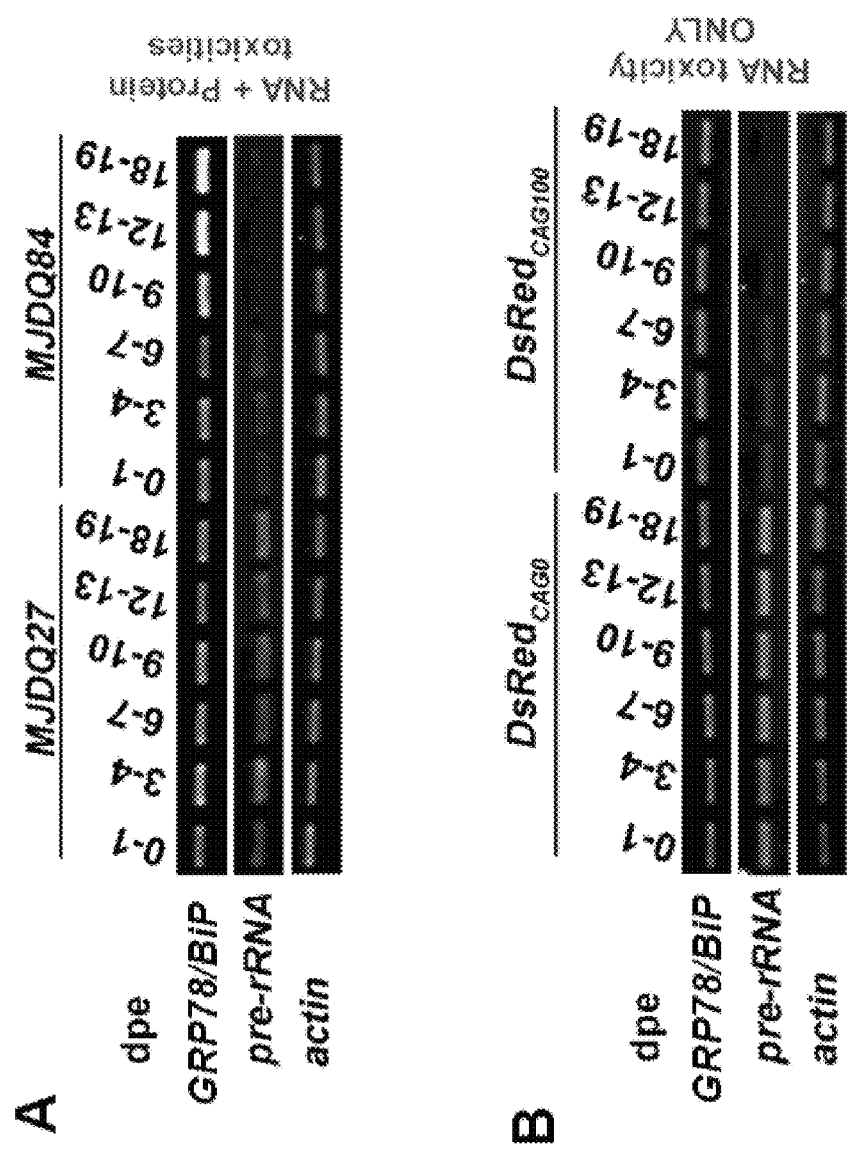
FIG. 5. Depicts the distinct stress responses induced by toxic expanded CAG-RNA and polyQ protein which can be differentiated by pre-rRNA and GRP78/BiP gene expression respectively in transgenic Drosophila and mammalian cell models. (A) A progressive downregulation of pre-rRNA transcription (indicates RNA toxicity) and induction of GRP78/BiP expression (indicates protein toxicity) was observed in flies expressing full-length expanded MJDQ84 RNA & protein, but not in control flies expressing full-length unexpanded MJDQ27 RNA & protein. (B) In contrast, only a progressive downregulation of pre-rRNA transcription but no induction of GRP78/BiP expression was observed in flies expressing expanded CAG RNA alone (without polyQ protein). "dpe" denotes days post eclosion. The CAG repeat sequence of the DsRed$_{CAG}$ constructs is located in the 3' UTR, thus expanded CAG RNA is produced but not expanded polyglutamine protein. Only RNA toxicity is observed in the DsRed$_{CAG}$ model. (C) The MJD$_{CAG}$ cell model displayed both GRP78/BiP induction and rRNA transcription dysregulation. The MJD$_{CAG}$ constructs express both expanded CAG RNA and polyglutamine protein. This model exhibits both RNA and protein toxicities. The MJD$_{CAA/G}$ construct only generates polyQ protein toxicity because the continuity of the expanded CAG sequence is disrupted which disrupts RNA toxicity. (D) Real-time PCR analysis of the effects of RNA and protein toxicity peptidylic inhibitors on pre-45s rRNA and GRP78/BiP expression in an MJD disease cell model. HEK293 cells expressing a polynucleotide encoding MJD$_{CAG78}$ reduced pre-45s rRNA transcription and induced GRP78/BiP expression. The introduction of P3 and QBP1 alone, or in combination, to MJD$_{CAG78}$-expressing cells restored pre-45s rRNA transcription and suppressed GRP78/BiP induction. In contrast, the P3MT5 and SCR inactive peptides did not demonstrate such suppressive effects. Cells expressing a polynucleotide encoding MJD$_{CAG27}$ served as a control. "SCR" and "P3MT5" represent scrambled QBP1 and mutant P3 peptides respectively.
Figure 5:
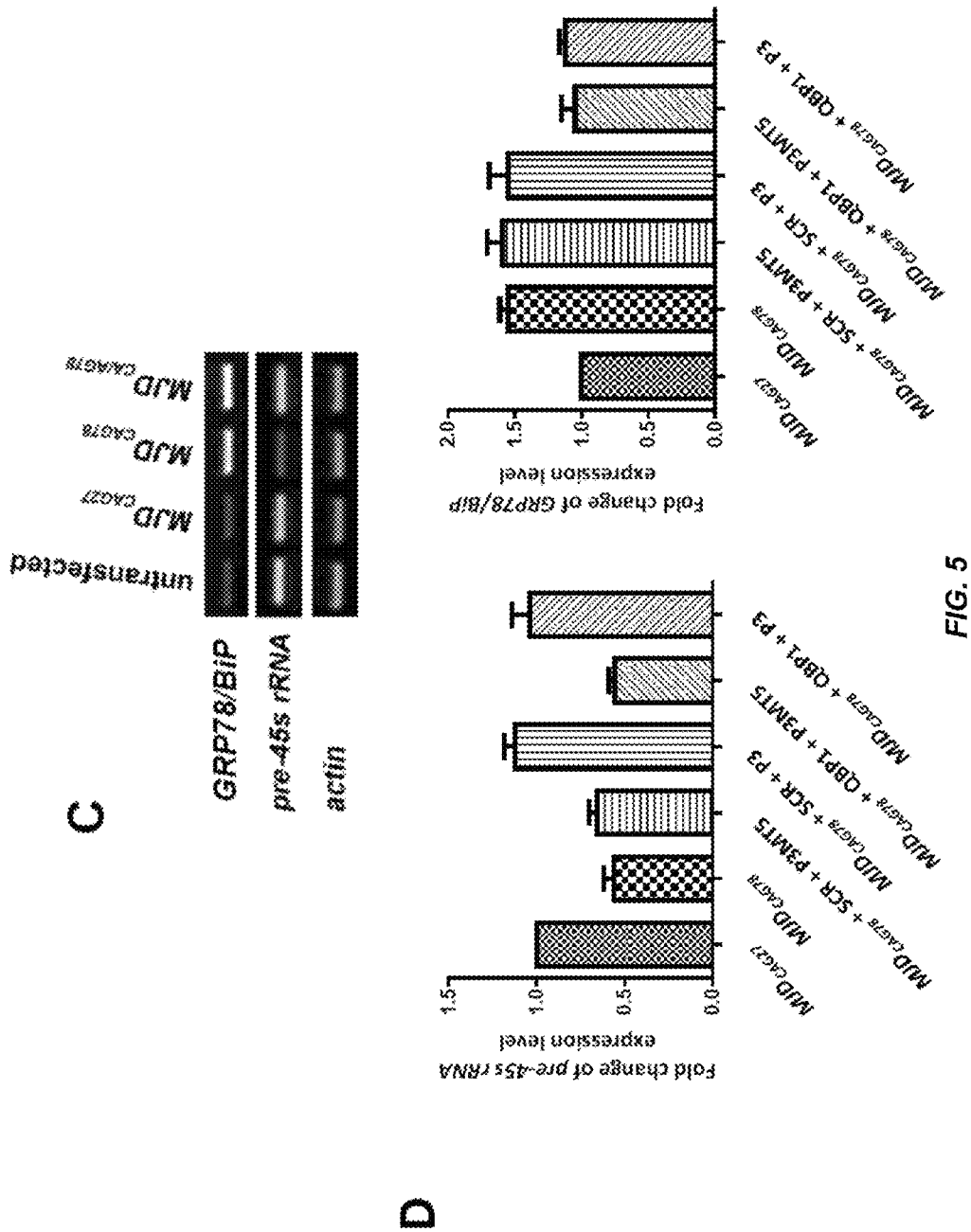

Expanded CAG-RNA Toxicity and PolyQ Toxicity can be Independently Monitored In Vivo Assays to determine toxicities that are respectively associated with expanded CAG RNA & expanded polyQ protein in both fly and cell polyQ disease models are provided (FIG. 5). The fly models all exhibit neurodegenerative phenotypes (Li L B, et al. 2008; Tsoi H, et al. 2012; Shieh S Y, et al. 2011). rRNA transcription was downregulated when expanded CAG RNA was expressed. In polyQ models that express both expanded CAG RNA and polyQ protein, the level of rRNA transcription is reduced in both the fly (FIG. 5A) and cell (FIG. 5C) models, and a similar progressive downregulation rRNA expression is observed in the DsRed$_{CAG}$ fly model which only exhibits expanded CAG RNA toxicity; FIG. 5B). This indicates that expression of expanded CAG RNA per se can cause downregulation of rRNA transcription. The MJD$_{CAA/G78}$ polyQ protein disease cell model can be used to determine whether rRNA transcription would be affected when only expanded polyQ protein was expressed. In the MJD$_{CAA/G78}$ cell model, the continuity of CAG repeat is disrupted, and it has been reported that expanded but interrupted CAA/G RNA is non-toxic. Because both "CAA" and "CAG" are codons for the amino acid glutamine, the number of glutamine residues in the MJD$_{CAG78}$ and MJD$_{CAA/G78}$ gene products would be the same. Thus, the expanded polyQ protein produced from the MJD$_{CAA/G78}$ construct would be the toxic species in the MJD$_{CAA/G78}$ model. We found that the expression level of rRNA transcription was not affected in the MJD$_{CAA/G78}$ model, thus indicating that the expression of expanded polyQ protein, in the absence of toxic expanded CAG RNA, does not affect rRNA transcription (FIG. 5C).

It has previously been reported that transcriptional upregulation of the endoplasmic reticulum chaperone protein gene GRP78/BiP is a key step of the unfolded protein response. Upregulation of GRP78/BiP expression has also been observed in polyQ diseases. The expression level of GRP78/BiP transcription in *Drosophila* (FIG. 5A) and cell (FIG. 5C) models of polyQ diseases was therefore measured. In flies, GRP78/BiP expression was progressively upregulated upon the expression of expanded polyQ protein (FIG. 5A). RNA toxicity is observed before protein toxicity as shown by the appearance of rRNA transcription downregulation before the induction of GRP78/BiP expression. In the DsRedCAG RNA toxicity fly model, no induction of GRP78/BiP was observed at any time point investigated (FIG. 5B). Similarly, induction of GFP78/BiP expression was observed in cells transfected with expanded MJD$_{CAG78}$ (protein+RNA toxicities) and MJD$_{CAA/G78}$ (protein toxicity only) constructs (FIG. 5C). These results indicate that GRP78/BiP induction only associates with polyQ protein toxicity. By measuring the expression levels of rRNA and GRP78/BiP, we are now able to differentiate between RNA and protein toxicities of polyQ diseases.

Example 10

Mutational Analysis of the P3 Peptide Nucleolar Stress Reduction Activity

Figure 6:
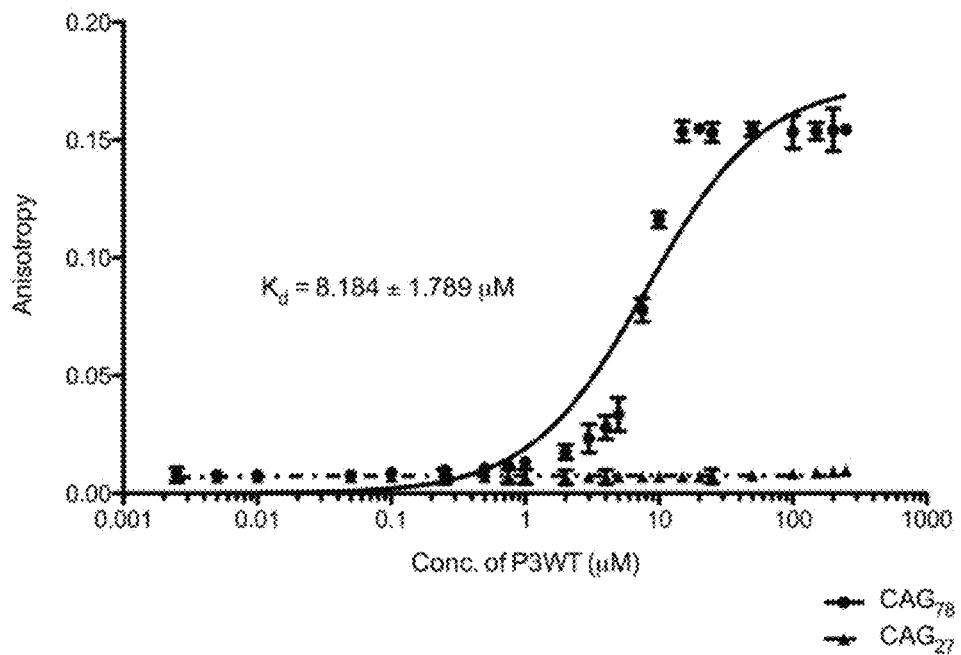
FIG. 6. Depicts the results of a fluorescence anisotropy experiment showing binding of CAG$_{78}$-RNA (SEQ ID NO:18) to peptide P3 (SEQ ID NO:6). "NCL P3WT represents wild-type NCL P3 peptide while "NCL P3MT5" represents NCL P3 peptide mutant number 5.

To further characterize P3 peptide action, the binding affinity of P3 towards expanded CAG-RNA was investigated. The expanded CAG-RNA CAG$_{78}$ (SEQ ID NO:18) was in vitro transcribed and then 5' labeled with a fluorescent group Cy3. Different concentrations of purified P3 (P3WT) were titrated with 10 μM labeled CAG$_{78}$ (SEQ ID NO:18) RNA, and the anisotropy of the RNA-peptide complex was measured. The value of anisotropy reflects the amount of the RNA-peptide complex formation (Luedtke N W, Tor Y, 2003). The detection of anisotropy indicates expanded CAG RNA interacts with P3. Based on the value of anisotropy obtained at different concentrations of CAG$_{78}$ (SEQ ID NO:18), a binding curve was plotted and the dissociation constant (Kd) of CAG$_{78}$/P3 was calculated to be 8.18 μM (FIG. 6). No binding between a labeled CAG$_{27}$ (SEQ ID NO:24) RNA and the wild-type P3 peptide was observed.

The results show that P3 peptide interacts physically with expanded CAG RNA. Further, P3 competes with full-length NCL protein for expanded CAG RNA. We are thus confident that P3 can be developed in to a therapeutic peptide inhibitor to reduce nucleolar stress induced by expanded CAG RNA expression in polyQ diseases.

Example 11

Mutational Analysis of the P3 Peptide Nucleolar Stress Reduction Activity

At the molecular level, polyQ diseases are caused by genomic CAG trinucleotide repeat expansion in the coding region of the disease genes (La Spada & Taylor, 2010) in which the CAG triplet repeats function as a codon for the glutamine amino acid. Upon gene transcription and protein translation, two primary toxic species, mRNA containing an expanded CAG repeat and protein carrying an expanded polyQ domain, are produced in the cells. (Fiszer & Krzyzosiak, 2009) Toxic expanded CAG RNA and polyQ protein have been reported to elicit neurotoxicities via multiple distinct pathogenic pathways (Bauer & Nukina, 2009; Shao & Diamond, 2007), including downregulation of the cellular protein quality control systems (Li, et al., 2008) and induction of nucleolar stress. (Tsoi, et al., 2012)

Figure 7:
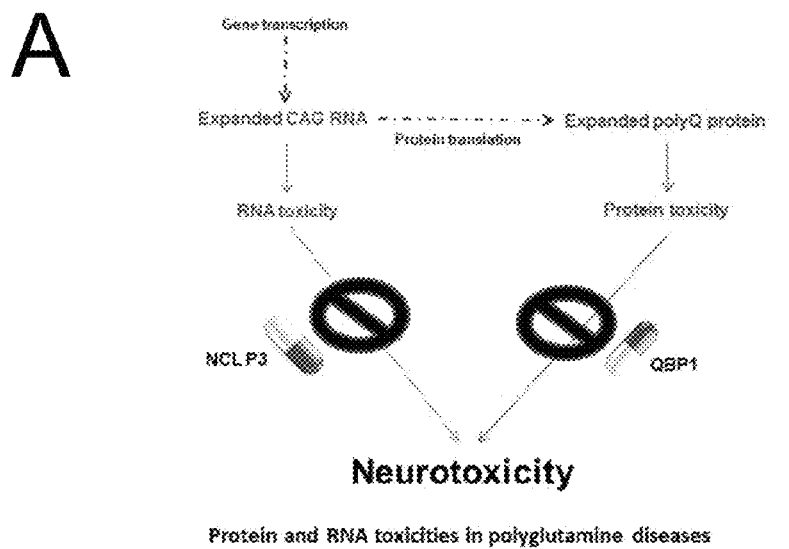
FIG. 7. (A) A co-treatment approach to target RNA and protein toxicities of polyQ diseases. (B) The combined effect of P3 and QBP1 peptides on suppressing neurodegeneration in a transgenic Drosophila polyQ model. Third instar larvae were incubated with corresponding peptides (100 µM each). Pseudopupil assay was performed on 0-3 day-old adult flies. The average number of rhabdomeres per ommatidium (single eye unit of the adult flies) is shown at the bottom left hand corner of each image. (C) Statistical analysis of (B). "WT" and "MT5" represent wildtype and mutant P3 peptides respectively. "SCR" denotes a scrambled sequence of QBP1. * represents $P<0.05$; ** represents $P<0.01$. Error bars represent standard deviation.
Figure 7:
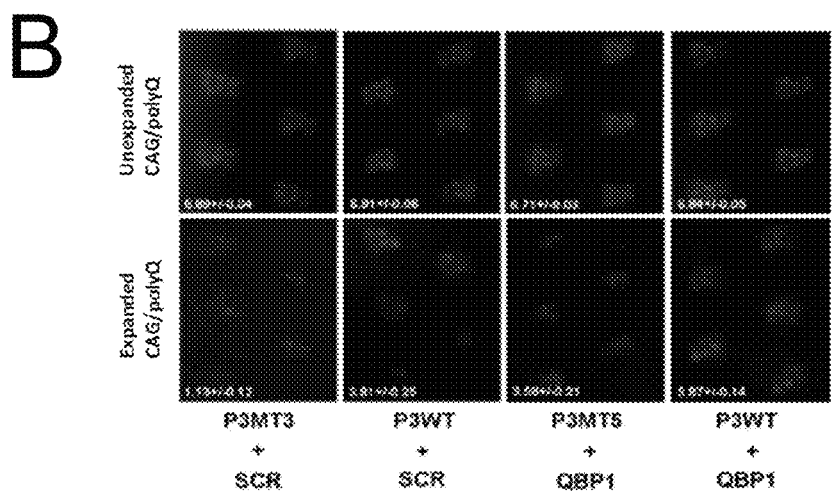
Figure 7:
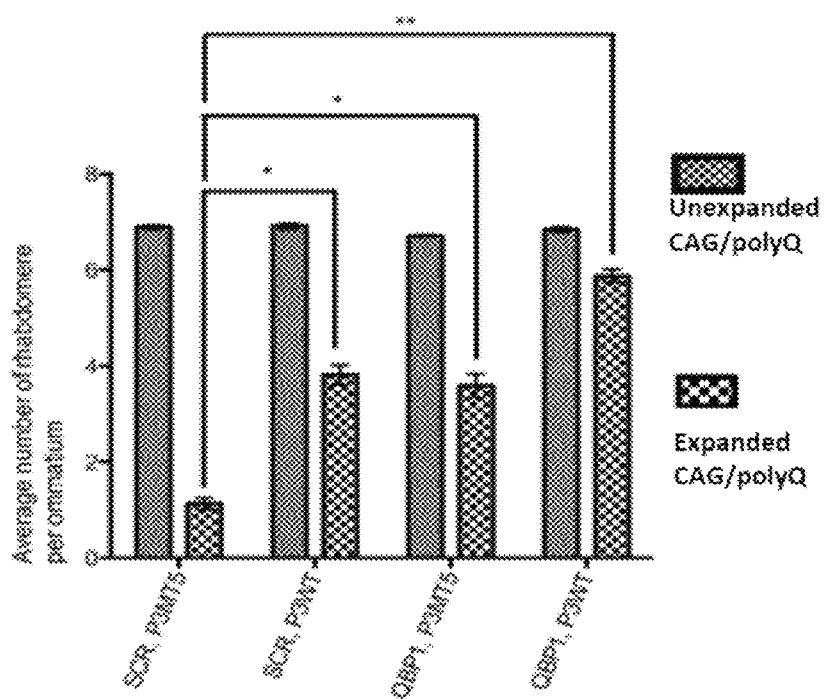

Because both expanded CAG RNA and polyQ protein contribute to neurotoxicity, a therapeutic strategy that simultaneously targets these toxic species would be ideal for treatment. A similar combined therapeutic approach was recently reported in cancer treatment (Suzuki, et al., 2013), indicating its therapeutic potential of this strategy. We have performed a pilot study to simultaneously target both the RNA and protein toxicities using a well-studied protein toxicity peptide QBP1 (Nagai, et al., 2000) and P3, and has obtained satisfactory suppression (FIG. 7A). We determined the suppressive effect of QBP1 and P3 separately, and together in a *Drosophila* polyQ disease model (Warrick, et al., 2005) exhibiting both RNA and protein toxicities. Our data show that both QBP1 and P3 exhibit substantial suppression when introduced independently into animals (FIGS. 7B&C). Moreover, we found the co-treatment of QBP1 and P3 to yield more potent suppression (FIGS. 7B&C). These findings show that the use of combined expanded CAG RNA and polyQ protein toxicity peptidylic inhibitors is a promising and novel therapeutic approach to polyQ disease treatment.

All patents, patent applications, and other publications, including GenBank Accession Numbers, cited in this application are incorporated by reference in the entirety for all purposes.

REFERENCES

Bauer, P. O.; Nukina, N. Journal of neurochemistry 2009, 110, 1737-1765.

Boulon S, Westman B J, Hutten S, Boisvert F M, Lamond A I. The nucleolus under stress. Molecular cell. 2010 Oct. 22; 40(2):216-27. PubMed PMID: 20965417. Pubmed Central PMCID: 2987465.

Chan W M, Tsoi H, Wu C C, Wong C H, Cheng T C, Li H Y, et al. Expanded polyglutamine domain possesses nuclear export activity which modulates subcellular localization and toxicity of polyQ disease protein via exportin-1. Human molecular genetics. 2011 May 1; 20(9):1738-50. PubMed PMID: 21300695.

Hong M, Lin M Y, Huang J M, Baumeister P, Hakre S, Roy A L, et al. Transcriptional regulation of the Grp78 promoter by endoplasmic reticulum stress: role of TFII-I and its tyrosine phosphorylation. The Journal of biological chemistry. 2005 Apr. 29; 280(17):16821-8. PubMed PMID: 15664986.

Hoozemans J J, Scheper W. Endoplasmic reticulum: the unfolded protein response is tangled in neurodegeneration. The international journal of biochemistry & cell biology. 2012 August; 44(8):1295-8. PubMed PMID: 22564438.

Fiszer, A.; Krzyzosiak, W. J. J Mol Med 2013, 91, 683-691.

Kalita K, Makonchuk D, Gomes C, Zheng J J, Hetman M. Inhibition of nucleolar transcription as a trigger for neuronal apoptosis. Journal of neurochemistry. 2008 Jun. 1; 105(6):2286-99. PubMed PMID: 18315559. Pubmed Central PMCID: 2909334.

Kouroku Y, Fujita E, Jimbo A, Kikuchi T, Yamagata T, Momoi M Y, et al. Polyglutamine aggregates stimulate ER stress signals and caspase-12 activation. Human molecular genetics. 2002 Jun. 15; 11(13):1505-15. PubMed PMID: 12045204.

Kressler D, Hurt E, Bassler J. Driving ribosome assembly. Biochimica et biophysica acta. 2010 June; 1803(6):673-83. PubMed PMID: 19879902.

Krzyzosiak W J, Sobczak K, Wojciechowska M, Fiszer A, Mykowska A, Kozlowski P. Triplet repeat RNA structure and its role as pathogenic agent and therapeutic target. Nucleic acids research. 2012 January; 40(1):11-26. PubMed PMID: 21908410. Pubmed Central PMCID: 3245940.

La Spada, A. R.; Taylor, J. P. Nature reviews. Genetics 2010, 11, 247-258.

Lee K S, You K H, Choo J K, Han Y M, Yu K. *Drosophila* short neuropeptide F regulates food intake and body size. The Journal of biological chemistry. 2004 Dec. 3; 279(49): 50781-9. PubMed PMID: 15385546.

Lee F K, Wong A K, Lee Y W, Wan O W, Chan H Y, Chung K K. The role of ubiquitin linkages on alpha-synuclein induced-toxicity in a *Drosophila* model of Parkinson's disease. Journal of neurochemistry. 2009 July; 110(1):208-19. PubMed PMID: 19457126.

Li, X.; Li, H.; Li, X. J. Brain research reviews 2008, 59, 245-252.

Li L B, Yu Z, Teng X, Bonini N M. RNA toxicity is a component of ataxin-3 degeneration in *Drosophila*. Nature. 2008 Jun. 19; 453(7198):1107-11. PubMed PMID: 18449188. Pubmed Central PMCID: 2574630.

Lindenboim L, Borner C, Stein R. Nuclear proteins acting on mitochondria. Biochimica et biophysica acta. 2011 April; 1813(4):584-96. PubMed PMID: 21130123.

Luedtke N W, Tor Y. Fluorescence-based methods for evaluating the RNA affinity and specificity of HIV-1 Rev-RRE inhibitors. Biopolymers. 2003 September; 70(1):103-19. PubMed PMID: 12925996.

Molhoek E M, van Dijk A, Veldhuizen E J, Haagsman H P, Bikker F J. Improved proteolytic stability of chicken cathelicidin-2 derived peptides by D-amino acid substitutions and cyclization. Peptides. 2011 May; 32(5):875-80. PubMed PMID: 21376095.

Nagai Y, Fujikake N, Ohno K, Higashiyama H, Popiel H A, Rahadian J, et al. Prevention of polyglutamine oligomerization and neurodegeneration by the peptide inhibitor QBP1 in *Drosophila*. Human molecular genetics. 2003 Jun. 1; 12(11):1253-9. PubMed PMID: 12761040.

Nagai Y, Tucker T., Ren H., Kenan D J, Henderson, B S, Keene J D, Strittmatter W J, Burke J R The Journal of Biological Chemistry 2000, 275, 10437-10442.

Orr H T, Zoghbi H Y. Trinucleotide repeat disorders. Annual review of neuroscience. 2007; 30:575-621. PubMed PMID: 17417937.

Popiel H A, Nagai Y, Fujikake N, Toda T. Protein transduction domain-mediated delivery of QBP1 suppresses polyglutamine-induced neurodegeneration in vivo. Molecular therapy: the journal of the American Society of Gene Therapy. 2007 February; 15(2):303-9. PubMed PMID: 17235308.

Popiel H A, Nagai Y, Fujikake N, Toda T. Delivery of the aggregate inhibitor peptide QBP1 into the mouse brain using PTDs and its therapeutic effect on polyglutamine disease mice. Neuroscience letters. 2009 Jan. 9; 449(2):87-92. PubMed PMID: 18603372.

Popiel H A, Burke J R, Strittmatter W J, Oishi S, Fujii N, Takeuchi T, et al. The Aggregation Inhibitor Peptide QBP1 as a Therapeutic Molecule for the Polyglutamine Neurodegenerative Diseases. Journal of amino acids. 2011; 2011: 265084. PubMed PMID: 22312459. Pubmed Central PMCID: 3268222.

Shao J, Diamond M I. Human molecular genetics 2007, 16 Spec No. 2, R115-R123.

Shieh S Y, Bonini N M. Genes and pathways affected by CAG-repeat RNA-based toxicity in *Drosophila*. Human molecular genetics. 2011 Dec. 15; 20(24):4810-21. PubMed PMID: 21933837. Pubmed Central PMCID: 3221540.

Suzuki, H.; Fukuhara, M.; Yamaura, T.; Mutoh, S.; Okabe, N.; Yaginuma, H.; Hasegawa, T.; Yonechi, A.; Osugi, J.; Hoshino, M.; Kimura, T.; Higuchi, M.; Shio, Y.; Ise, K.; Takeda, K.; Gotoh, M. Journal of translational medicine 2013, 11, 97.

Svensen N, Walton J G, Bradley M. Peptides for cell-selective drug delivery. Trends in pharmacological sciences. 2012 April; 33(4):186-92. PubMed PMID: 22424670.

Tsoi H, Lau T C, Tsang S Y, Lau K F, Chan H Y. CAG expansion induces nucleolar stress in polyglutamine diseases. Proceedings of the National Academy of Sciences of the United States of America. 2012 Aug. 14; 109(33): 13428-33. PubMed PMID: 22847428. Pubmed Central PMCID: 3421186.

Wang S, Kaufman R J. The impact of the unfolded protein response on human disease. The Journal of cell biology. 2012 Jun. 25; 197(7):857-67. PubMed PMID: 22733998.

Warrick J M, Morabito L M, Bilen J, Gordesky-Gold B, Faust L Z, Paulson H L, Bonini N M. Molecular Cell 2005, 18, 37-48.

Wojciechowska M, Krzyzosiak W J. Cellular toxicity of expanded RNA repeats: focus on RNA foci. Human molecular genetics. 2011 Oct. 1; 20(19):3811-21. PubMed PMID: 21729883. Pubmed Central PMCID: 3168290.

Wolfe K J, Cyr D M. Amyloid in neurodegenerative diseases: friend or foe? Seminars in cell & developmental biology. 2011 July; 22(5):476-81. PubMed PMID: 21458579. Pubmed Central PMCID: 3182296.

---

What is claimed is:

1. An isolated polypeptide comprising (1) a core sequence that is a fragment of nucleolin (NCL) of less than 50 amino acids and comprises SEQ ID NO:6 and (2) a heterologous amino acid sequence located at the N-terminus or the C-terminus of the core sequence, provided that the polypeptide does not comprise the full length NCL.

2. The polypeptide of claim 1, wherein the heterologous amino acid sequence is located at the N-terminus of the core sequence.

3. The polypeptide of claim 2, wherein the heterologous amino acid sequence is located at the C-terminus of the core sequence.

4. The polypeptide of claim 2, wherein there are two heterologous amino acid sequences, the first located at the N-terminus and the second located at the C-terminus of the core sequence.

5. The polypeptide of claim 1, wherein the heterologous amino acid sequence comprises a purification tag, a membrane translocation sequence, or a nucleolar localization signal sequence.

6. A composition comprising the polypeptide of claim 1 and a pharmaceutically acceptable excipient.

7. The composition of claim 6, wherein the composition further comprises a peptide consisting of the amino acid sequence set forth in SEQ ID NO:15.

8. An isolated nucleic acid comprising a polynucleotide sequence encoding the polypeptide of claim 1.

9. An expression cassette comprising the nucleic acid of claim 8.

10. An isolated host cell comprising the expression cassette of claim 9.

11. A composition comprising the nucleic acid of claim 8 and a pharmaceutically acceptable excipient.

12. A kit for inhibiting proliferation or reducing cytotoxicity of a cell, the kit comprising the composition of claim 6.

13. A method of reducing (CAG)n-mediated toxicity in a cell, the method comprising contacting the cell with a composition comprising an effective amount of the polypeptide of claim 1.

14. The method of claim 13, wherein the cell is in a patient's body.

15. The method of claim 14, wherein the patient suffers from Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17.

16. The method of claim 14, wherein the contacting step is performed by oral administration, or subcutaneous, intramuscular, intravenous, intraperitoneal, or intratumor injection.

17. The method of claim 13, wherein the composition further comprises a peptide of the amino acid sequence set forth in SEQ ID NO: 15.

18. A method of reducing (CAG)n-mediated toxicity in a cell, the method comprising contacting the cell with a composition comprising an effective amount of the nucleic acid of claim 8.

19. The method of claim 18, wherein the cell is in a patient's body.

20. The method of claim 19, wherein the patient suffers from Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17.

21. The method of claim 19, wherein the contacting step is performed by oral administration, or subcutaneous, intramuscular, intravenous, intraperitoneal, or intratumor injection.

22. The method of claim 19, wherein the composition further comprises a peptide of the amino acid sequence set forth in SEQ ID NO: 15.

* * * * *

SEQUENCE LISTING

<160> NUMBER OF SEQ ID NOS: 25

<210> SEQ ID NO 1
<211> LENGTH: 77
<212> TYPE: PRT
<213> ORGANISM: Artificial Sequence
<220> FEATURE:
<223> OTHER INFORMATION: synthetic nucleolin RNA recognition motif (RRM) domain RRM1

<400> SEQUENCE: 1

```
Phe Asn Leu Phe Ile Gly Asn Leu Asn Pro Asn Lys Ser Val Ala Glu
1               5                   10                  15

Leu Lys Val Ala Ile Ser Glu Pro Phe Ala Lys Asn Asp Leu Ala Val
            20                  25                  30

Val Asp Val Arg Thr Gly Thr Asn Arg Lys Phe Gly Tyr Val Asp Phe
        35                  40                  45

Glu Ser Ala Glu Asp Leu Glu Lys Ala Leu Glu Leu Thr Gly Leu Lys
    50                  55                  60

Val Phe Gly Asn Glu Ile Lys Leu Glu Lys Pro Lys Gly
65                  70                  75
```

<210> SEQ ID NO 2
<211> LENGTH: 74
<212> TYPE: PRT
<213> ORGANISM: Artificial Sequence
<220> FEATURE:
<223> OTHER INFORMATION: synthetic nucleolin RNA recognition motif (RRM) domain RRM2

<400> SEQUENCE: 2

```
Arg Thr Leu Leu Ala Lys Asn Leu Ser Phe Asn Ile Thr Glu Asp Glu
1               5                   10                  15

Leu Lys Glu Val Phe Glu Asp Ala Leu Glu Ile Arg Leu Val Ser Gln
            20                  25                  30

Asp Gly Lys Ser Lys Gly Ile Ala Tyr Ile Glu Phe Lys Ser Glu Ala
        35                  40                  45

Asp Ala Glu Lys Asn Leu Glu Glu Lys Gln Gly Ala Glu Ile Asp Gly
    50                  55                  60

Arg Ser Val Ser Leu Tyr Tyr Thr Gly Glu
65                  70
```

<210> SEQ ID NO 3
<211> LENGTH: 75
<212> TYPE: PRT
<213> ORGANISM: Artificial Sequence
<220> FEATURE:
<223> OTHER INFORMATION: synthetic nucleolin RNA recognition motif (RRM) domain RRM3

<400> SEQUENCE: 3

```
Lys Thr Leu Val Leu Ser Asn Leu Ser Tyr Ser Ala Thr Glu Glu Thr
1               5                   10                  15

Leu Gln Glu Val Phe Glu Lys Ala Thr Phe Ile Lys Val Pro Gln Asn
            20                  25                  30

Gln Gln Gly Lys Ser Lys Gly Tyr Ala Phe Ile Glu Phe Ala Ser Phe
        35                  40                  45
```

```
Glu Asp Ala Lys Glu Ala Leu Asn Ser Cys Asn Lys Met Glu Ile Glu
    50                  55                  60

Gly Arg Thr Ile Arg Leu Glu Leu Gln Gly Pro
65                  70                  75

<210> SEQ ID NO 4
<211> LENGTH: 7
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P1

<400> SEQUENCE: 4

Ala Lys Asn Leu Pro Tyr Lys
 1               5

<210> SEQ ID NO 5
<211> LENGTH: 14
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P2

<400> SEQUENCE: 5

Arg Val Ala Ser Lys Asp Gly Lys Ser Lys Gly Ile Ala Asp
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P3

<400> SEQUENCE: 6

Asp Gly Lys Ser Lys Gly Ile Ala Tyr Ile Glu Phe Lys
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P4

<400> SEQUENCE: 7

Asp Ala Leu Glu Ile Arg Leu Val Ser Gln Arg Gly Lys
 1               5                  10

<210> SEQ ID NO 8
<211> LENGTH: 14
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P5

<400> SEQUENCE: 8
```

```
Val Pro Gln Asn Gln Asn Gly Lys Ser Lys Gly Tyr Ala Phe
1               5                   10
```

<210> SEQ ID NO 9
<211> LENGTH: 9
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P6

<400> SEQUENCE: 9

```
Arg Glu Ile Glu Gly Arg Ala Ile Arg
1               5
```

<210> SEQ ID NO 10
<211> LENGTH: 13
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P3MT1

<400> SEQUENCE: 10

```
Asp Gly Ala Ser Lys Gly Ile Ala Tyr Ile Glu Phe Lys
1               5                   10
```

<210> SEQ ID NO 11
<211> LENGTH: 13
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P3MT2

<400> SEQUENCE: 11

```
Asp Gly Lys Ser Ala Gly Ile Ala Tyr Ile Glu Phe Lys
1               5                   10
```

<210> SEQ ID NO 12
<211> LENGTH: 13
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P3MT3/MTa

<400> SEQUENCE: 12

```
Asp Gly Lys Ser Lys Gly Ile Ala Ala Ile Glu Phe Lys
1               5                   10
```

<210> SEQ ID NO 13
<211> LENGTH: 13
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P3MT4/MTb

<400> SEQUENCE: 13

```
Asp Gly Lys Ser Lys Gly Ile Ala Tyr Ile Glu Ala Lys
1               5                   10
```

```
<210> SEQ ID NO 14
<211> LENGTH: 13
<212> TYPE: PRT
<213> ORGANISM: Artificial Sequence
<220> FEATURE:
<223> OTHER INFORMATION: synthetic nucleolin RNA recognition motif
      (RRM), RRM domain of nucleolin, RRM-related sequence core amino
      acid sequence P3MT5/MTc

<400> SEQUENCE: 14

Asp Gly Lys Ser Lys Gly Ile Ala Ala Ile Glu Ala Lys
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: synthetic polyQ-mediated toxicity inhibitor
      peptide QBP1

<400> SEQUENCE: 15

Ser Asn Trp Lys Trp Trp Pro Gly Ile Phe Asp
 1               5                  10

<210> SEQ ID NO 16
<211> LENGTH: 300
<212> TYPE: RNA
<213> ORGANISM: Artificial Sequence
<220> FEATURE:
<223> OTHER INFORMATION: synthetic CAG triplet nucleotide repeat RNA
<220> FEATURE:
<221> NAME/KEY: repeat_region
<222> LOCATION: (30)...(300)
<223> OTHER INFORMATION: CAG repeats from positions 30-300 may be
      present or absent

<400> SEQUENCE: 16
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca gcagcagcag cagcagcagc agcagcagca gcagcagcag   240
cagcagcagc agcagcagca gcagcagcag cagcagcagc agcagcagca gcagcagcag   300

<210> SEQ ID NO 17
<211> LENGTH: 180
<212> TYPE: RNA
<213> ORGANISM: Artificial Sequence
<220> FEATURE:
<223> OTHER INFORMATION: synthetic CAG triplet nucleotide repeat RNA
<220> FEATURE:
<221> NAME/KEY: repeat_region
<222> LOCATION: (30)...(180)
<223> OTHER INFORMATION: CAG repeats from positions 30-180 may be
      present or absent

<400> SEQUENCE: 17
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180

<210> SEQ ID NO 18
<211> LENGTH: 234
<212> TYPE: RNA
<213> ORGANISM: Artificial Sequence
```

```
<220> FEATURE:
<223> OTHER INFORMATION: synthetic CAG-78 triplet nucleotide repeat RNA

<400> SEQUENCE: 18
cagcagcagc agcagcagca gcagcagcag cagcagcagc agcagcagca gcagcagcag     60
cagcagcagc agcagcagca gcagcagcag cagcagcagc agcagcagca gcagcagcag    120
cagcagcagc agcagcagca gcagcagcag cagcagcagc agcagcagca gcagcagcag    180
cagcagcagc agcagcagca gcagcagcag cagcagcagc agcagcagca gcag          234

<210> SEQ ID NO 19
<211> LENGTH: 234
<212> TYPE: RNA
<213> ORGANISM: Artificial Sequence
<220> FEATURE:
<223> OTHER INFORMATION: synthetic CUG-78 triplet nucleotide repeat RNA

<400> SEQUENCE: 19
cugcugcugc ugcugcugcu gcugcugcug cugcugcugc ugcugcugcu gcugcugcug     60
cugcugcugc ugcugcugcu gcugcugcug cugcugcugc ugcugcugcu gcugcugcug    120
cugcugcugc ugcugcugcu gcugcugcug cugcugcugc ugcugcugcu gcugcugcug    180
cugcugcugc ugcugcugcu gcugcugcug cugcugcugc ugcugcugcu gcug          234

<210> SEQ ID NO 20
<211> LENGTH: 41
<212> TYPE: DNA
<213> ORGANISM: Artificial Sequence
<220> FEATURE:
<223> OTHER INFORMATION: synthetic primer T7CAGF for CAG-78

<400> SEQUENCE: 20
taaacgactc actataggga gaagaagcct actttgaaaa a                         41

<210> SEQ ID NO 21
<211> LENGTH: 18
<212> TYPE: DNA
<213> ORGANISM: Artificial Sequence
<220> FEATURE:
<223> OTHER INFORMATION: synthetic primer CAGR for CAG-78

<400> SEQUENCE: 21
ctgtcctgat aggtcccg                                                   18

<210> SEQ ID NO 22
<211> LENGTH: 42
<212> TYPE: DNA
<213> ORGANISM: Artificial Sequence
<220> FEATURE:
<223> OTHER INFORMATION: synthetic primer T7CUGF for CUG-78

<400> SEQUENCE: 22
taatacgact cactataggg agaagacacg actatccagg gc                        42

<210> SEQ ID NO 23
<211> LENGTH: 18
<212> TYPE: DNA
<213> ORGANISM: Artificial Sequence
<220> FEATURE:
<223> OTHER INFORMATION: synthetic primer CUGR for CUG-78

<400> SEQUENCE: 23
cttcggatga aactttt                                                    18
```

```
<210> SEQ ID NO 24
<211> LENGTH: 81
<212> TYPE: RNA
<213> ORGANISM: Artificial Sequence
<220> FEATURE:
<223> OTHER INFORMATION: synthetic CAG-27 triplet nucleotide repeat RNA

<400> SEQUENCE: 24
cagcagcagc agcagcagca gcagcagcag cagcagcagc agcagcagca gcagcagcag      60
cagcagcagc agcagcagca g                                                81

<210> SEQ ID NO 25
<211> LENGTH: 30
<212> TYPE: RNA
<213> ORGANISM: Artificial Sequence
<220> FEATURE:
<223> OTHER INFORMATION: synthetic 10 repeats of CAG triplet nucleotide
      repeat RNA

<400> SEQUENCE: 25
cagcagcagc agcagcagca gcagcagcag                                       30
```